(12) United States Patent
Li et al.

(10) Patent No.: US 9,394,308 B2
(45) Date of Patent: Jul. 19, 2016

(54) INHIBITING THE TRANSIENT RECEPTOR POTENTIAL A1 ION CHANNEL

(71) Applicant: Merck Sharp & Dohme Corp., Rahway, NJ (US)

(72) Inventors: Qingyi Li, Somerville, MA (US); Lily Cheng, Chestnut Hill, MA (US); Christopher M. Liu, Somerville, MA (US); Iwona E. Wrona, Sharon, MA (US); Blaise S. Lippa, Acton, MA (US); Chester A. Metcalf, III, Needham, MA (US); Andrew J. Jackson, Waltham, MA (US); Lauren M. Chapman, Pasadena, CA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/160,333

(22) Filed: Jan. 21, 2014

(65) Prior Publication Data

US 2014/0206650 A1    Jul. 24, 2014

Related U.S. Application Data

(60) Provisional application No. 61/754,103, filed on Jan. 18, 2013, provisional application No. 61/754,132, filed on Jan. 18, 2013, provisional application No. 61/780,836, filed on Mar. 13, 2013.

(51) Int. Cl.
*C07D 473/08* (2006.01)
*C07F 9/6561* (2006.01)

(52) U.S. Cl.
CPC .......... *C07D 473/08* (2013.01); *C07F 9/65616* (2013.01)

(58) Field of Classification Search
CPC .................................................... C07D 473/08
USPC .......................................................... 544/269
See application file for complete search history.

(56) References Cited

U.S. PATENT DOCUMENTS

| | | |
|---|---|---|
| 7,582,658 B2 | 9/2009 | Miyoshi et al. |
| 7,671,061 B2 | 3/2010 | Moran et al. |
| 8,163,761 B2 | 4/2012 | Ng et al. |
| 2007/0219222 A1 | 9/2007 | Moran et al. |
| 2010/0249154 A1 | 9/2010 | Ng et al. |
| 2011/0151018 A1 | 6/2011 | Garrity et al. |
| 2012/0083474 A1 | 4/2012 | Berthelot et al. |
| 2012/0157411 A1 | 6/2012 | Kumar et al. |
| 2012/0316136 A1 | 12/2012 | Khairatkar-Joshi et al. |
| 2013/0274273 A1* | 10/2013 | Metcalf et al. ............ 514/263.21 |
| 2014/0158116 A1* | 6/2014 | Chong et al. ............. 128/200.14 |
| 2014/0163048 A1* | 6/2014 | Barker et al. ............ 514/263.21 |

FOREIGN PATENT DOCUMENTS

| | | |
|---|---|---|
| RU | 2352338 C2 | 4/2009 |
| WO | WO-2005/059107 A2 | 6/2005 |
| WO | WO2009/002933 A1 | 12/2008 |
| WO | WO2009144548 A1 | 12/2009 |
| WO | WO2010004390 A1 | 1/2010 |
| WO | WO2010/075353 A1 | 7/2010 |
| WO | WO2010109287 A1 | 9/2010 |
| WO | WO2010141805 A1 | 9/2010 |
| WO | WO2010/138879 A1 | 12/2010 |
| WO | WO2011043954 A1 | 4/2011 |
| WO | WO2011114184 A1 | 9/2011 |
| WO | WO2012050512 A1 | 4/2012 |
| WO | WO2013/023102 A1 | 2/2013 |
| WO | WO-2014/026073 A1 | 2/2014 |
| WO | WO-2014/113671 A1 | 7/2014 |

OTHER PUBLICATIONS

Ibuprofen. Drugs.com, 2011. < http://www.drugs.com/ibuprofen.html>.*
Albuterol Inhalation. Drugs.com, 2012. < http://www.drugs.com/albuterol.html>.*
Wermuth, Camille. Molecular Variations Based on Isoteric Replacements. The Practice of Medicinal Chemistry. Academic Press, 1996. pp. 203-237.*
Bessac, et al: Breathtaking TRP Channels: TRPA1 and TRPV1 in Airway Chemosensation and Reflex Control; Physiology; 2008, vol. 23, pp. 360-370.
Nassini, et al: Transient Receptor Potential Ankyrin 1 Channel Localized to Non-Neuronal Airway Cells Promotes Non-Neurogenic Inflammation; PLoS One; Aug. 2012, vol. 7, Issue 8, e42454; 12 pages.
Nassenstein, et al: Expression and function of the ion channel TRPA1 in vagal afferent nerves innervating mouse lungs; J Physiology; 2008; vol. 586; pp. 1595-1604.
Panke, et al: A cell-based impedance assay for monitoring transient receptor potential (TRP) ion channel activity; Biosensors and Bioelectronics; 2011, vol. 26, pp. 2376-2382.
Mishra, et al: The Cells and Circuitry for Itch Responses in Mice; Science; 2013, vol. 340, pp. 968-971.
Wilson, et al: The Ion Channel TRPA1 is Required for Chronic Itch; J. Neuroscience; 2013, vol. 33:22, pp. 9283-9294.
Roberson, et al: Activity-dependent silencing reveals functionally distinct itch-generating sensory neurons; Nature Neuroscience; 2013; vol. 16, pp. 910-918.
International Search Report for Application No. PCT/US2013/054246. Dated Dec. 26, 2013. 10 pages.
Andersson, et al: TRPA1 mediates spinal antinociception induced by acetaminophen and the cannabinoid Δ9-tetrahydrocannabiorcol; Nature Communications, 2:551, (2011), 11 pages.
Banke, The dilated TRPA1 channel pore state is blocked by amiloride and analogues; Brain Research, 1381, pp. 21-30 (2011).
Banner, et al: TRP channels: Emerging targets for respiratory disease; Pharmacology & Therapeutics; vol. 130, pp. 371-384 (2011).
Baraldi, et al: Transient Receptor Potential Ankyrin 1 (TRPA1) Channel as Emerging Target for Novel Analgesics and Anti-Inflammatory Agents; J.Med.Chem, 53, pp. 5085-5107 (2010).
Brouwers, et al: In vitro behavior of a phosphate ester prodrug of amprenavirin human intestinal fluids and in the Caco-2 system: Illustration of intraluminal supersaturation; International Journal of Pharmaceutics, vol. 336, pp. 302-309 (2007).

(Continued)

*Primary Examiner* — Golam M M Shameem
*Assistant Examiner* — Laura Daniel
(74) *Attorney, Agent, or Firm* — Keith D. MacMillan; John C. Todaro

(57) ABSTRACT

This disclosure describes novel compounds and pharmaceutical compositions for inhibiting the TRPA1 ion channel and/or medical conditions related to TRPA1, such as pain and respiratory conditions.

8 Claims, 15 Drawing Sheets

(56) References Cited

OTHER PUBLICATIONS

Caceres: A sensory neuronal ion channel essential for airway inflammation and hyperREactivity in asthma; PNAS, Jun. 2, 2009, vol. 106, No. 22, pp. 9909-9104.
Cao, De-Shou, et al: Expression of Transient Receptor Potential Ankyrin 1 (TRPA1) and Its Role in Insulin Release from Rat Pancreatic Beta Cells; PloS One, 2012, vol. 7, Issue 5, 10 pages.
Chen, Jun, et al: Selective blockade of TRPA1 channel attenuates pathological pain without altering noxious cold sensation or body temperature regulation; Pain, vol. 152, pp. 1165-1172 (2011).
Del Camino, Donato, et. al: TRPA1 Contributes to Cold Hypersensitivity; Journal of Neuroscience, 30(45), pp. 15165-15174 (Nov. 10, 2010).
Facchinetti, Fabrizio, et al: The Rising Role of TRPA1 in Asthma; The Open Drug Discovery Journal, 2, pp. 71-80 (2010).
Fanger, Christopher, M., et. al: TRPA1 as an Analgesic Target; The Open Drug Discovery Journal, 2, pp. 64-70 (2010).
Fechner, Jorg, et al: Pharmacokinetics and Clinical Pharmacodynamics of the new Propofol Prodrug GPI 15715 in Volunteers; Anesthesiology, vol. 99, No. 2, 303-313 (Aug. 2003), Retracted.
Fernandes, Es, et al: The functions of TRPA1 and TRPV1: moving away from sensory nerves; British Journal of Pharmacology, 166, 510-521 (2012).
Fischer, James, H., et al: Fosphenytoin Clinical Pharmacokinetics and Comparative Advantages in the Acute Treatment of Seizures; Clin Pharmacokinet, 42(1), 33-58 (2003).
Gijsen, Harrie, J.M. et al: Tricyclic 3,4-dihydropyrimidine-2-thione derivatives as potent TRPA1 antagonists; Bioorganic & Medicinal Chemistry Letters, 22, 797-800 (2012).
Gijsen, Harrie, J.M. et al: Tricyclic 3,4-dihydropyrimidine-2-thione derivatives as potent TRPA1 antagonists; Johnson & Johnson, Poster (2012).
International Search Report, PCT/US2012/050210, dated Sep. 11, 2012, 6 pages.
Indian Patent Application 2512-MUM-2008 date stamped Nov. 27, 2009, entitled "Uracil and 6-Azauracil Derivatives as TRPA1 Modulators," 41 pages.
Usmani, Omar, et al: Theobromine inhibits sensory nerve activation and cough; FASEB Journal, Feb. 2005, vol. 19 (2), pp. 231-233.
Koivisto, et al: Inhibiting TRPA1 ion channel reduces loss of cutaneous nerve fiber function in diabetic animals: Sustained activation of the TRPA1 channel contributes to the pathogenesis of peripheral diabetic neuropathy; Pharmacological Research; 2012, vol. 65(1), pp. 149-158
Krise, Jeffrey, P., et al: Prodrugs of phosphates, phosphonates, and phosphinates; Advanced Drug Delivery Reviews, 19, pp. 287-310 (1996).
Krise, Jeffrey, P., et al: Novel Prodrug Approach for Tertiary Amines: Synthesis and Preliminary Evaluation of N-Phosphonooxymethyl Prodrugs; J. Med. Chem., vol. 42, pp. 3094-3100 (1999).
Li, Weixing, et al: Identification of GS 4104 as an Orally Bioavailable Prodrug of the Influenza Virus Neuraminidase Inhibitor GS 4071; Antimicrobial Agents and Chemotherapy, vol. 42, No. 3., pp. 647-653 (Mar. 1998).
Yagi, Shigenori, et al: Development of Anti-Influenza Virus Drugs I: Improvement of Oral Absorption and in Vivo Anti-Influenza Activity of Stachyflin and Its Derivatives; Pharmaceutical Research, vol. 16, No. 7, pp. 1041-1046, (1999).
McNamara, Colleen, R., et al: TRPA1 mediates formalin-induced pain; PNAS vol. 104, No. 33, pp. 13525-13530, Aug. 14, 2007.
Mills, James, E.J., et al: SAR mining and its application to the design of TRPA1 antagonists; MedChemComm, 2012, vol. 3, pp. 174-178.
Moran, Magdalene, M., et al: Transient Receptor Potential Ankyrin 1 as a Target for Perioperative Pain Management; Anesthesiology, vol. 117, pp. 8-9 (2012).
Moran, Magdalene, et. al: Transient receptor potential channels as therapeutic targets; Nature Reviews, vol. 10, pp. 601-620 (Aug. 2011).
Morozowich, et al: Clindamycin 2-Phosphate, A Prodrug of Clindamycin; Prodrugs: Biotechnology Pharmaceutical Aspects, vol. V, pp. 509-519.
Wei, Hong, et al: Transient Receptor Potential Ankyrin 1 Ion Channel Contributes to Guarding Pain and Mechanical Hypersensitivity in a Rat Model of Postoperative Pain; Anesthesiology, vol. 117, pp. 137-148 (2012).
Vallin, K.S.A., et al: N-1-alkyl-2-oxo-2-aryl amides as novel antagonists of the TRPA1 receptor; Bioorganic & Medicinal Chemistry Letters; 2012, vol. 22(17), pp. 5485-5492 (Manuscript copy).
Pochopin, Nancy, et al: Pharmacokinetics of Dapsone and Amino Acid Prodrugs of Dapsone; Drug Metabolism and Disposition, vol. 2 (5), pp. 770-775 (1994).
Pochopin, Nancy, et al: Amino acid derivatives of dapsone as water-soluble prodrugs; International Journal of Pharmaceutics, vol. 121, pp. 157-167 (1995).
Press Release dated Aug. 30, 2010, "Glenmark announces the Discovery of a novel chemical entity GRC 17536, a potential first-in-class molecule globally", Glenmark Pharmaceuticals Ltd., 2 pages.
Rech, Jason, et al: Recent advances in the biology and medicinal chemistry of TRPA1; Future Science, vol. 2(5), pp. 843-858 (2010).
Reilly, Regina: TRPA1 as a Pain Target: Challenges and Progress; Abbott, Cambridge Healthtech Institute International, (2009), 21 pages.
Ryckmans, Thomas, et al: Design and pharmacological evaluation of PF-4840154, a non-electrophilic reference agonist of the TrpA1 channel; Bioorganic & Medicinal Chemistry Letters, vol. 21, pp. 4857-4859 (2011).
Stella: A case for prodrugs: Fosphenytoin; Advanced Drug Delivery Reviews, vol. 19, pp. 311-330 (1996).
Stella, et al:Aqueous Solubility and Dissolution Rate Does Not Adequately Predict in Vivo Performance: A Probe Utilizing Some N-Acyloxymethyl Phenytoin Prodrugs, J. Pharmaceutical Sciences, vol. 88, No. 8, Aug. 1999, 5 pages.
Stella, Valentino, J., et al: Prodrug strategies to overcome poor water solubility, Advanced Drug Delivery Reviews, 59, pp. 677-694 (2007).
Stella, Valentino, J., et al: Site-specific drug delivery via prodrgus; Design of Prodrugs, pp. 177-198 (1985).
Heppelmann, et al: Inhibitory effect of amiloride and gadolinium on fine afferent nerves in the rat knee: evidence of mechanogated ion channels in joints; Experimental Brain Research; 2005, vol. 167, No. 1, pp. 114-118.
Klement, et al: Characterization of a Ligand Binding Site in the Human Transient Receptor Potential Ankyrin 1 Pore; Biophysical Journal, Feb. 2013, vol. 104, pp. 798-806.
Lu, et al: TRPA1b, a functional human vanilloid receptor splice variant; Mol. Pharmacol.; Apr. 2005; vol. 67(4), pp. 1119-1127.
Nagata, et al: Nociceptor and Hair Cell Transducer Properties of TRPA1, a Channel for Pain and Hearing; The Journal of Neuroscience, 2005, vol. 25, No. 16, pp. 4052-4062.
Pfizer, Prospective use: TrpA1. 42nd National Organic Chemistry Symposium, Princeton, NJ, Jun. 5-9, 2011, Poster.
Abbott, F.V. et al., The formalin test: scoring properties of the first and second phases of the pain response in rats, Pain, 60(1):91-102 (1995).
Abraham, W.M., Animal models of asthma, Asthma and Rhinitis, Edited by Busse, W.W. and Holgate, S.T., Oxford: Blackwell Science, Chapter 78: 1205-1227 (2000).
Banker, M.J. et al., Development and Validation of a 96-Well Equilibrium Dialysis Apparatus for Measuring Plasma Protein Binding, Journal of Pharmaceutical Sciences, 92(5): 967-74 (2003).
Bautista, D.M. et al., TRPA1 Mediates the Inflammatory Actions of Environmental Irritants and Proalgesic Agents, Cell, 124 (6):1269-1282 (2006).
Brennan, T.J. et al., Characterization of a rat model of incisional pain, Pain, 64(3): 493-501 (1996).
Dubuisson, D. and Dennis, S.G., The Formalin Test: A quantitative study of the analgesic effects of morphine, meperidine, and brain stem stimulation in rats and cats, Pain, 4(2): 161-74 (1977).
International Search Report for PCT/US2014/012049, 4 pages (May 9, 2014).

(56) References Cited

OTHER PUBLICATIONS

Jordt, S.E. et al., Mustard oils and cannabinoids excite sensory nerve fibres through the TRP channel ANKTM1, Nature, 427(6971): 260-265 (2004).

Katsura, H. et al., Antisense knock down of TRPA1, but not TRPM8, alleviates cold hyperalgesia after spinal nerve ligation in rats, Exploratory Neurology, 200: 112-123 (2006).

Kerns, E.H., High throughput physicochemical profiling for drug discovery, Journal of Pharmaceutical Sciences, 90(11): 1838-1858 (2001).

Kremeyer, B. et al., A gain-of-function mutation in TRPA1 causes familial episodic pain syndrome, Neuron, 66(5):671-680 (2010).

Kwan, K.Y. et al., TRPA1 Contributes to Cold, Mechanical, and Chemical Nociception but is Not Essential for Hair-Cell Transduction, Neuron, 50: 277-289 (2006).

Materazzi, S., TRPA1 and TRPV4 mediate paclitaxel-induced peripheral neuropathy in mice via a glutathione-sensitive mechanism, Pflugers Arch., European Journal of Physiology, 463(4):561-569 (2012).

Obata, K. et al., TRPA1 induced in sensory neurons contributes to cold hyperalgesia after inflammation and nerve injury, Journal of Clinical Investigation, 115(9): 2393-2401 (2005).

Written Opinion for PCT/US2012/050210, 7 pages (Nov. 9, 2012).

Written Opinion for PCT/US2013/054246, 7 pages (Dec. 26, 2013).

\* cited by examiner

Table 1a (Comparative Compounds)

| Compound No. | Compound Structure | Human TRPA1 IC50 Inward Current (nM) | pH 4.0 aqueous solubility (mg/mL) | pH 7.4 aqueous solubility (mg/mL) | pH 9.0 aqueous solubility (mg/mL) |
|---|---|---|---|---|---|
| Comparator 1 | 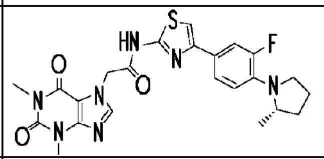 | A | | | |
| Comparator 2 | 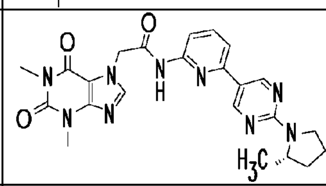 | C | 0.009 | 0.007 | 0.010 |
| Comparator 3 | 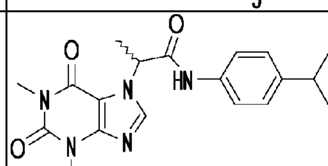 | D | | | |
| Comparator 4 | 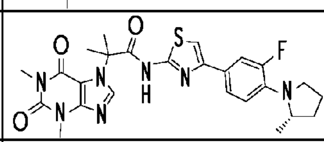 | D | | | |
| Comparator 5 | 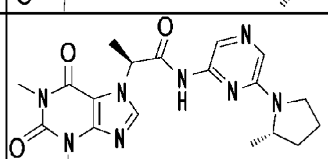 | D | | | |
| Comparator 6 | 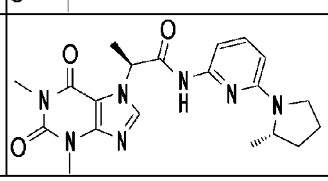 | D | | | |

Table 1b

| Compound No. | Compound Structure | Human TRPA1 IC50 Inward Current (nM) | pH 4.0 aqueous solubility (mg/mL) | pH 7.4 aqueous solubility (mg/mL) | pH 9.0 aqueous solubility (mg/mL) |
|---|---|---|---|---|---|
| 1-A | 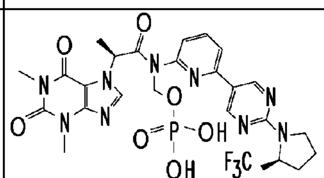 | D | >1 | >1 | >1 |
| 1-B | 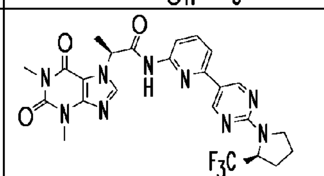 | A | 0.054 | 0.044 | 0.049 |
| 1-C | 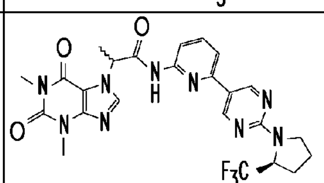 | A | | | |
| 1-D | 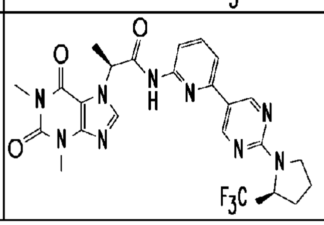 | D | | | |

FIG.1B

Table 1c

| Compound No. | Compound Structure | Human TRPA1 IC50 Inward Current (nM) | pH 4.0 aqueous solubility (mg/mL) | pH 7.4 aqueous solubility (mg/mL) | pH 9.0 aqueous solubility (mg/mL) |
|---|---|---|---|---|---|
| 5-S | 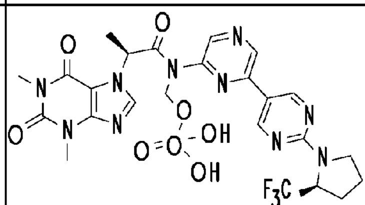 | A | >1 | >1 | >1 |
| 5-T | 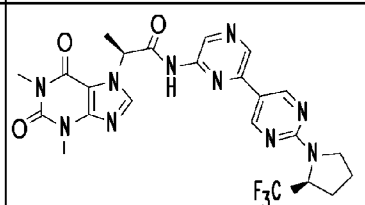 |  | 0.005 | 0.005 | 0.007 |
| 5-U | 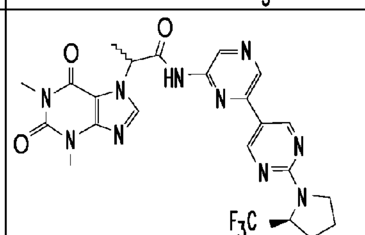 | A |  |  |  |
| 5-V | 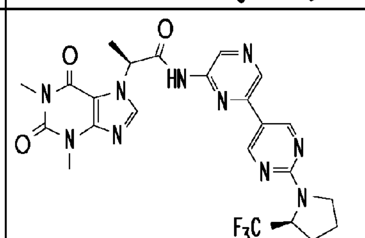 | D |  |  |  |

Table 1d

| Compound No. | Compound Structure | Human TRPA1 IC50 Inward Current (nM) | pH 4.0 aqueous solubility (mg/mL) | pH 7.4 aqueous solubility (mg/mL) | pH 9.0 aqueous solubility (mg/mL) |
|---|---|---|---|---|---|
| 2-E | 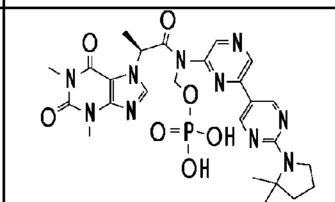 | D | >1 | >1 | >1 |
| 2-F | 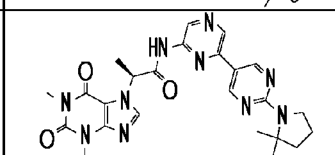 | A | 0.006 | 0.006 | 0.006 |
| 2-G | 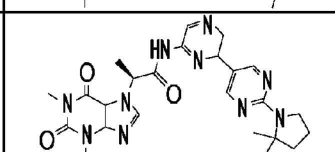 | D | | | |
| 2-H | 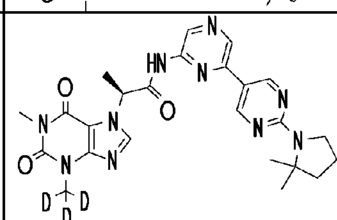 | A | | | |
| 2-I | 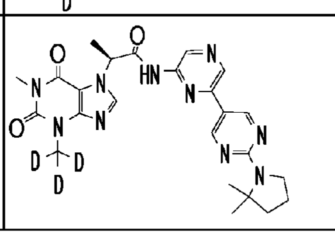 | D | | | |

Table 1e

| Compound No. | Compound Structure | Human TRPA1 IC50 Inward Current (nM) | pH 4.0 aqueous solubility (mg/mL) | pH 7.4 aqueous solubility (mg/mL) | pH 9.0 aqueous solubility (mg/mL) |
|---|---|---|---|---|---|
| 3-J | 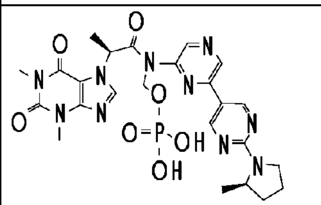 | D | >1 | >1 | >1 |
| 3-K | 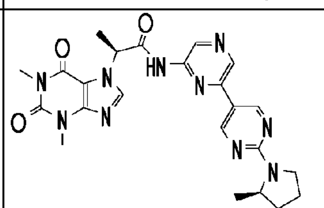 | B | 0.049 | 0.038 | 0.048 |
| 3-L | 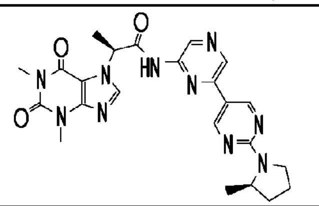 | D | | | |
| 3-M | 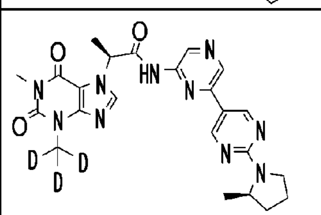 | A | | | |
| 3-N | 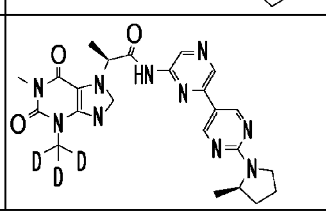 | D | | | |

FIG. 1E

Table 1f

| Compound No. | Compound Structure | Human TRPA1 IC50 Inward Current (nM) |
|---|---|---|
| 4-P | 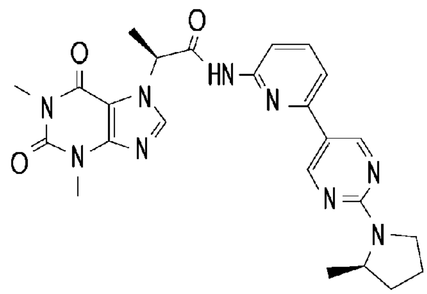 | B |
| 4-Q | 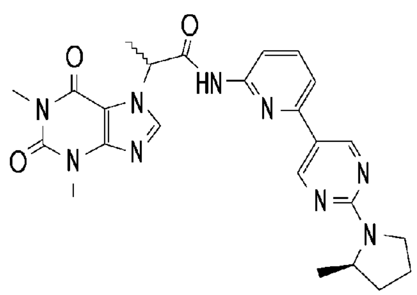 | B |
| 4-R | 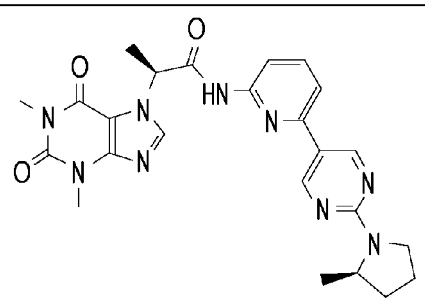 | D |

Table 2
| Compound ID | Compound | Minimal Efficacious Dose of Compound in Formalin Model (mg/kg IV) | Dose (mg/kg) | Duration of Pain Behavior (sec) | Error (sec) |
|---|---|---|---|---|---|
| Vehicle | | -- | -- | 88.6 | 4.3 |
| 1-A | 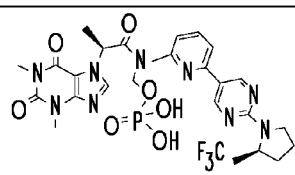 | 3 | 0.3 | 77.7 | 3.8 |
| | | | 1.2 | 43.3 | 8.4 |
| | | | 4 | 19.8 | 8 |
| 1-B | 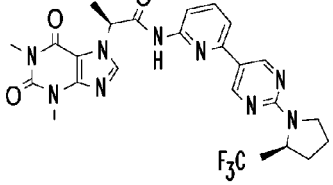 | 1 | 3 | 6.1 | 5.5 |
| | | | 10 | 0.3 | 0.3 |
| 2-E | 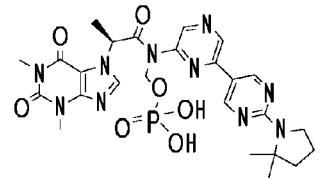 | 3 | 0.3 | 80.4 | 9.3 |
| | | | 1 | 77 | 10 |
| | | | 3 | 15.1 | 7.9 |
| 2-F | 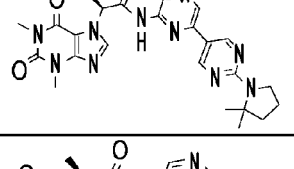 | 1 | 0.3 | 67.5 | 11 |
| | | | 1 | 7 | 4.4 |
| | | | 3 | 5 | 3 |
| 3-J | 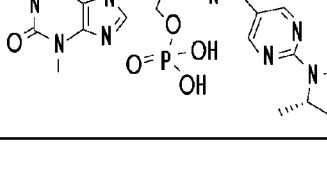 | 3 | 3 | 39.7 | 10.9 |
| | | | 10 | 1.6 | 1.1 |
FIG.2A-1

| Compound ID | Compound | Minimal Efficacious Dose of Compound in Formalin Model (mg/kg IV) | Dose (mg/kg) | Duration of Pain Behavior (sec) | Error (sec) |
|---|---|---|---|---|---|
| 3-K |  | 1 | 3 | 13.5 | 6.9 |
|  |  |  | 10 | 2.6 | 1.4 |
|  |  |  | 30 | 3.4 | 1.8 |
| 5-S |  | 3 | 0.3 | 69.8 | 3.9 |
|  |  |  | 1 | 52.3 | 13.8 |
|  |  |  | 3 | 8.4 | 6.3 |
|  |  |  | 10 | 0 | 0 |

Figure 3

Table 3

| Compound | Compound | Single IV Bolus Dose (mg/kg) | Alterations in LFT | LFT: % upper normal range ALT/AST serum levels |
|---|---|---|---|---|
| Comparator 1 | [structure] | 50 | ↑ | 1000% / 514% |
| 1-A | [structure] | 100 | ↔ | <100% / <100% |
| 2-E | [structure] | 100 | ↔ | <100% / <100% |
| 3-J | [structure] | 130 | ↔ | <100% / <100% |
| 5-S | [structure] | 100 | ↔ | <100% / <100% |

Figure 4: General Synthesis of Intermediates Useful for the Synthesis of Compounds of Formula (I)

Figure 5A: General Synthesis of Compounds of Formula (I) wherein R¹ is hydrogen

Figure 5B: General Synthesis of compounds of Formula (I), wherein $R^1$ is $CH_2$-phosphate Figure 6: Formation of the HCl Salt of a Compound of Formula (I) wherein R¹ is hydrogen

INHIBITING THE TRANSIENT RECEPTOR POTENTIAL A1 ION CHANNEL

RELATED APPLICATIONS

This application is related to U.S. Provisional Application No. 61/754,103, filed Jan. 18, 2013, U.S. Provisional Application No. 61/754,132, filed Jan. 18, 2013, and U.S. Provisional Application No. 61/780,836, filed Mar. 13, 2013. These applications are incorporated herein by reference in their entireties.

TECHNICAL FIELD

The present invention relates to pharmaceutical compositions and methods for the treatment of pain, respiratory conditions, as well as inhibiting the Transient Receptor Potential A1 ion channel (TRPA1).

BACKGROUND

Transient Receptor Potential A1 (herein, "TRPA1") is a non-selective cation channel related to pain sensation in humans. TRPA1 is found in sensory neurons and functions as a signal transduction receptor linking inflammation to pain. Activation of TRPA1 is believed to cause pain by inducing firing of nociceptive neurons and driving central sensitization in the spinal cord. TRPA1 stimulation can also increase firing of sensory neurons, leading to the release of pro-inflammatory neuropeptides such as NK-A, substance P and CGRP (which induce vasodilation and help recruit immune cells). A variety of endogenous reactive compounds produced during inflammation activate TRPA1 (including 4-hydroxynonenal released during liposome peroxidation; cyclopentane prostaglandins synthesized by COX enzymes; hydrogen peroxide produced by oxidative stress). Activation of TRPA1 also sensitizes TRPA1 to cold. Furthermore, a gain-of-function mutation in TRPA1 causes familial episodic pain syndrome; patients suffering from this condition have episodic pain that may be triggered by cold. Thus, TRPA1 is considered to play a role in pain related to nerve damage, cold allodynia, and inflammatory pain.

Compounds that inhibit the TRPA1 ion channel can be useful, for example, in treating conditions ameliorated, eliminated or prevented by inhibition of the TRPA1 ion channel. For example, pharmaceutical compositions that inhibit TRPA1 can be used to treat pain. Inhibition of TRPA1 (e.g., by genetic ablation and chemical antagonism) has been shown to result in reduced pain behavior in mice and rats. Knockout mice lacking functional TRPA1 have diminished nociceptive responses to TRPA1 activators (including AITC, formalin, acrolein, 4-hydroxynonenal) and, in addition, have greatly reduced thermal and mechanical hypersensitivity in response to the inflammatory mediator bradykinin (e.g., Kwan, K. Y. et al. Neuron 2006, 50, 277-289; Bautista, D. M. et al. Cell 2006, 124, 1269-1282). In animal pain models, down regulation of TRPA1 expression by gene specific antisenses prevented and reversed cold hyperalgesia induced by inflammation and nerve injury (See, e.g., Obata, K. et al., Journal of Clinical Investigation 2005, 115, 2393-2401; Jordt, S. E. et al., Nature 2004, 427, 260-265; Katsura, H. et al., Exploratory Neurology 2006, 200, 112-123). TRPA1 inhibitor compounds are effective in a variety of rodent pain models. TRPA1 inhibitors have been shown to reduce mechanical hypersensitivity and cold allodynia following inflammation induced by Complete Freund's Adjuvant (without altering normal cold sensation in naïve animals) and also to improve function in the rat mono-iodoacetate osteoarthritis model. Materazzi, S et al., European Journal of Physiology 2012, 463(4):561-9; Wei H et al., Anesthesiology 2012, 117 (1):137-48; Koivisto, A et al., Pharmacol Res. 2012, 65(1): 149-58. TRPA1 inhibitor compounds have demonstrated reduced pain behavior in rodents injected with AITC (mustard oil), formalin, cinnamaldehyde, acrolein, and other TRPA1 activators.

A compound for inhibiting the TRPA1 ion channel is disclosed in PCT/US2009/069146 and published as WO2010/075353A1 on Jul. 1, 2010:

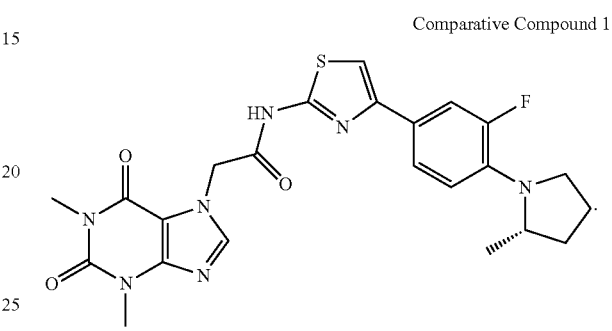

Comparative Compound 1

However, while Comparative Compound 1 is disclosed as an inhibitor of the TRPA1 ion channel, the administration of Comparative Compound 1 was later found to elevate the serum biomarkers of hepatotoxicity in certain animal studies (e.g., as disclosed in Example 5 herein).

Another compound for inhibiting the TRPA1 ion channel is disclosed in U.S. patent application No. 61/521,705 filed on Aug. 9, 2011:

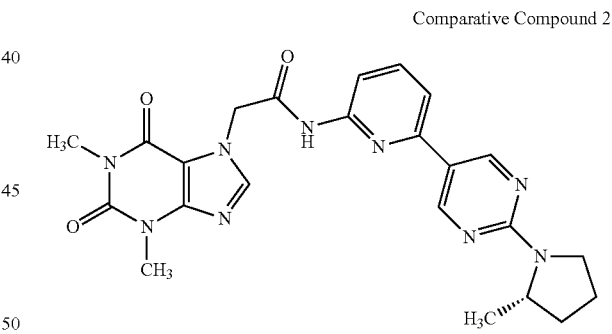

Comparative Compound 2

While Comparative Compound 2 is an inhibitor of the TRPA1 ion channel that did not elevate the serum biomarkers of hepatotoxicity in the animal studies (as disclosed in Example 5 herein), Comparative Compound 2 has undesirably low aqueous solubility for formulation in intravenous administration (see data in Example 2 herein).

Accordingly, there remains an unmet medical need for novel compounds with greater aqueous solubility than Comparative Compound 2 (e.g., use in intravenous pharmaceutical compositions) that are therapeutically effective in the treatment of pain, respiratory conditions, and/or the inhibition of the TRPA1 ion channel, without producing serum biomarkers of hepatotoxicity observed when administering the Comparative Compound 1 (e.g., in the method of Example 5 disclosed herein). Such novel compounds preferably inhibit the TRPA1 ion channel in vivo, without producing serum biomarkers of hepatotoxicity.

SUMMARY

Compounds of Formula (I) are useful for the treatment of pain and/or to inhibit the TRPA1 ion channel:

Formula (I)

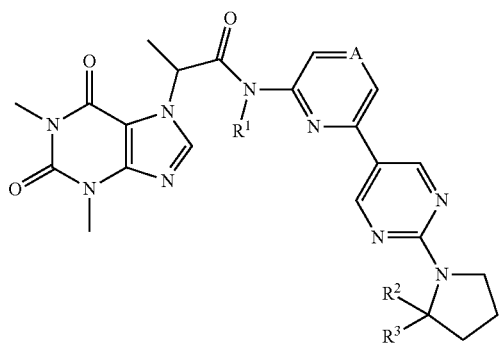

wherein
$R^1$ is hydrogen or —$CH_2$—$R^{1a}$, wherein $R^{1a}$ is a phosphate moiety;
$R^2$ is hydrogen or $CH_3$;
$R^3$ is $CH_3$ or $CF_3$; and
A is N or CH.

Particularly preferred compounds of Formula (I) are compounds of Formula (Ia):

Formula (Ia)

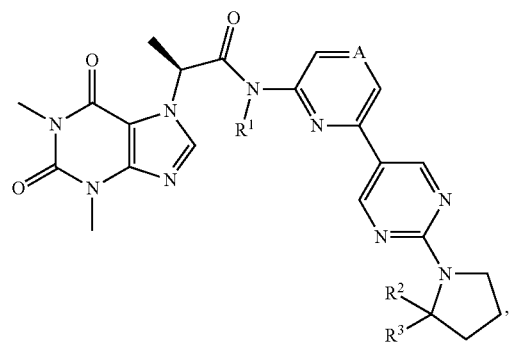

where $R^1$, $R^2$, $R^3$ and A are as defined for Formula (I).

The present invention is based in part on the unexpected discovery that compounds of Formula (Ia) can inhibit the TRPA1 ion channel (according to the method of Example 2 disclosed herein) without elevating serum biomarkers of hepatotoxicity (according to the method of Example 5 disclosed herein). In addition, compounds of Formula (Ia) where $R^1$ is —$CH_2$—$R^{1a}$, and $R^{1a}$ is a phosphate moiety have improved aqueous solubility compared to Comparative Compound 2 (including compounds with aqueous solubility suitable for pharmaceutical compositions formulated for intravenous administration). Upon administration, compounds of Formula (Ia) where $R^1$ is —$CH_2$—$R^{1a}$, and $R^{1a}$ is a phosphate moiety can be administered to therapeutically reduce symptoms of pain. Administration of compounds of Formula (Ia) where $R^1$ is —$CH_2$—$R^{1a}$, and $R^{1a}$ is a phosphate moiety can result in the in vivo conversion into compounds of Formula (Ia) where $R^1$ is H in amounts effective to therapeutically treat pain (e.g., by inhibiting the TRPA1 ion channel). Compounds of Formula (I) (e.g., Formula (Ia)) are also useful in amounts effective to therapeutically treat respiratory conditions such as obstructive diseases, e.g., chronic obstructive pulmonary disease (COPD), asthma (e.g., Cold induced asthma, exercise-induced asthma, allergy-induced asthma, and occupational asthma), and cough, preferably a condition responsive to a TRPA1 inhibitor.

In addition, compounds of Formula (Ia) are useful in the manufacture of a pharmaceutical composition formulated for intravenous administration to treat pain (e.g., a prodrug compound of Formula (Ia) where $R^1$ is —$CH_2$—$R^{1a}$, and $R^{1a}$ is a phosphate moiety that can be converted within the blood of a mammal to a compound of Formula (Ia) where $R^1$ is H after administration).

BRIEF DESCRIPTION OF THE DRAWINGS

FIG. 3 (Table 3) is a data table showing results from acute tolerability testing of certain compounds of Formula (I) (obtained by the method of Example 5).

DETAILED DESCRIPTION

Figure 1A:
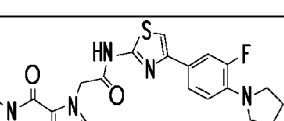
FIG. 1 (as FIGS. 1A to 1F) is a collection of data tables showing in vitro measurements of the inhibition of TRPA1 (measured by the method of Example 1) and the aqueous solubility of certain compounds of Formula (I) (measured by the method of Example 2).
Figure 1A:
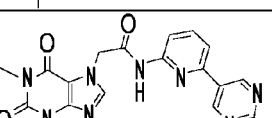
Figure 1A:
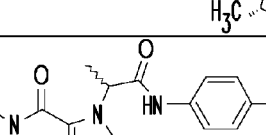
Figure 1A:
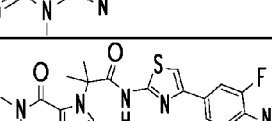
Figure 1A:
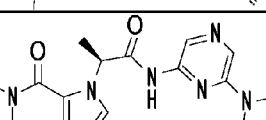
Figure 1A:
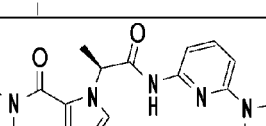
Figure 1C:
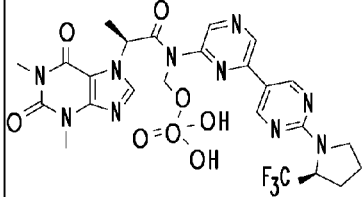
Figure 1C:
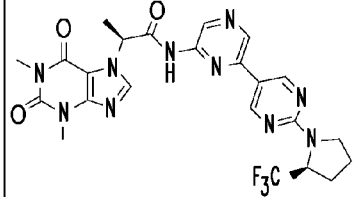
Figure 1C:
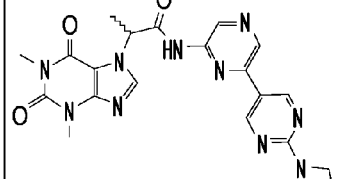
Figure 1C:
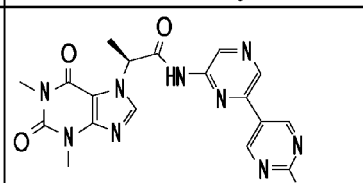
Figure 1D:
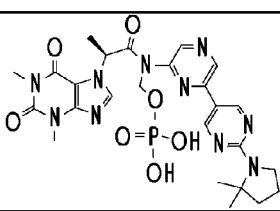
Figure 1D:
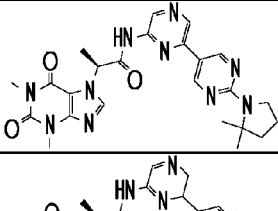
Figure 1D:
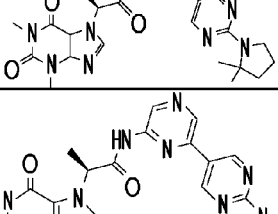
Figure 1D:
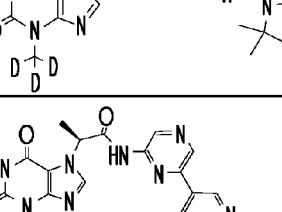
Figure 1D:
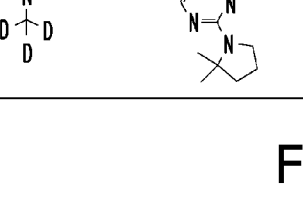
Figure 1F:
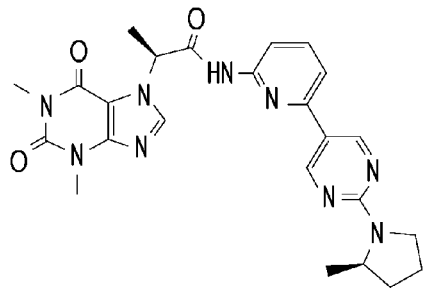
Figure 1F:
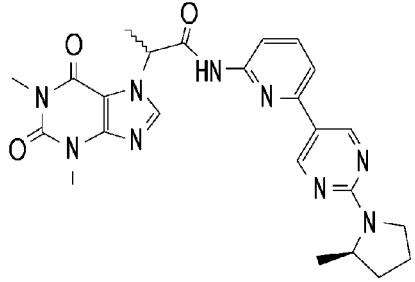
Figure 1F:
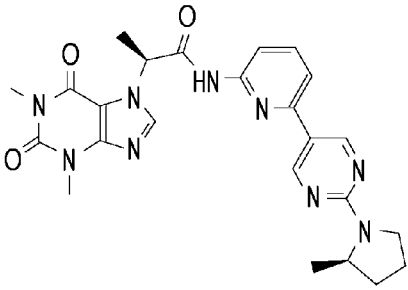

Unless otherwise indicated herein, the compounds of Formula (I) can include one or more stereoisomers of Formula (Ia) or Formula (Ib), or mixtures thereof (e.g., a racemic mixture of Formula (Ic)):

Formula (I)

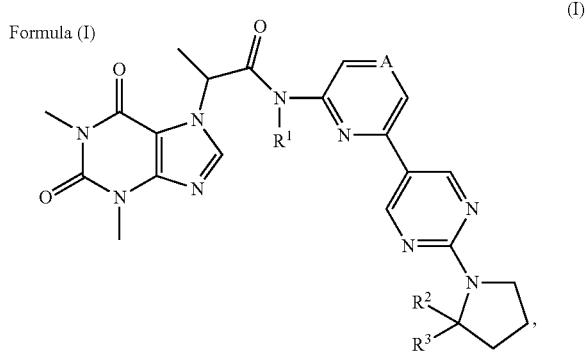

Formula (Ia)

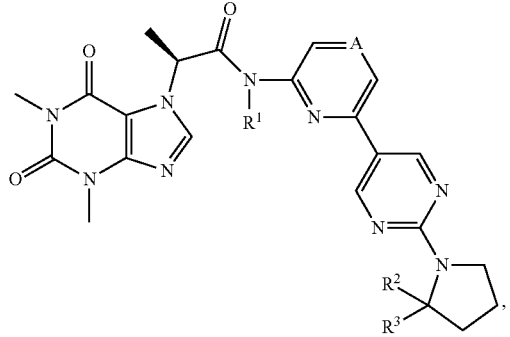

Formula (Ib)

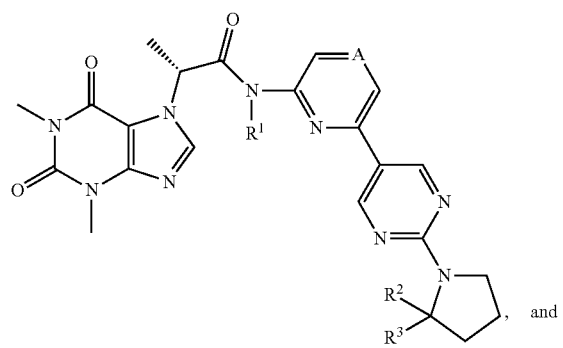

and

Formula (Ic)

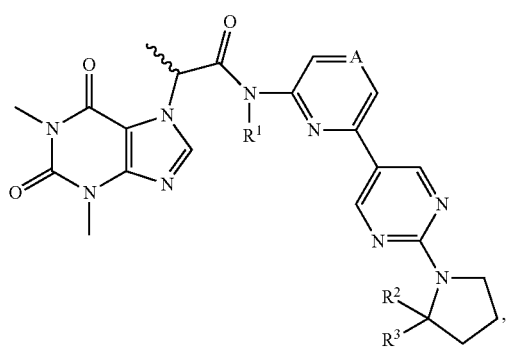

wherein $R^1$ is hydrogen or —$CH_2$—$R^{1a}$, wherein $R^{1a}$ is a phosphate moiety;

$R^2$ is hydrogen or $CH_3$;

$R^3$ is $CH_3$ or $CF_3$; and

A is N or CH.

The compounds of Formula (I) can include molecules having one or more chiral centers. For example, unless otherwise stated, a composition of Formula (I) can contain various amounts of stereoisomers of Formula (Ia) and (Ib). Formula (Ic) describes a composition of Formula (I) having a racemic mixture of the stereoisomers of Formula (Ia) and (Ib). Unless otherwise indicated, a composition comprising a compound of Formula (Ia) preferably contains a therapeutically effective amount of the compound having the stereochemistry indicated in Formula (Ia) (e.g., an enantiomeric excess of a particular compound of Formula (Ia) over the corresponding stereoisomer of Formula (Ib)).

Unless otherwise indicated, the phosphate moiety at $R^1$ can exist in equilibrium in different chemical forms, with the relative proportion of any particular form depending on the pH of the chemical environment.

When a stereoisomer is depicted by name or structure, it is to be understood that the stereoisomeric purity of the named or depicted stereoisomer is at least 60%, 70%, 80%, 90%, 99% or 99.9% pure by weight. Stereoisomeric purity is determined by dividing the weight of the named or depicted stereoisomer in the mixture by the total weight of all stereoisomers in the mixture.

When a compound is designated by a name or structure that indicates a single enantiomer, unless indicated otherwise, the compound is at least 60%, 70%, 80%, 90%, 99% or 99.9% optically pure (also referred to as "enantiomerically pure"). Optical purity is the weight in the mixture of the named or depicted enantiomer divided by the total weight in the mixture of both enantiomers.

In addition, compounds of Formula (I) can include one or more isotopes of the atoms present in Formula (I). For example, compounds of Formula (I) can include: those in which H (or hydrogen) is replaced with any isotopic form of hydrogen including $^1H$, $^2H$ or D (Deuterium), and $^3H$ (Tritium); those in which C is replaced with any isotopic form of carbon including $^{12}C$, $^{13}C$, and $^{14}C$; those in which O is replaced with any isotopic form of oxygen including $^{16}O$, $^{17}O$ and $^{18}O$; those in which N is replaced with any isotopic form of nitrogen including $^{13}N$, $^{14}N$ and $^{15}N$; those in which P is replaced with any isotopic form of phosphorous including $^{31}P$ and $^{32}P$; those in which S is replaced with any isotopic form of sulfur including $^{32}S$ and $^{35}S$; those in which F is replaced with any isotopic form of fluorine including $^{19}F$ and $^{18}F$; and the like. In a preferred embodiment, compounds represented by Formula (I) comprise isomers of the atoms therein in their naturally occurring abundance. In particular embodiments of the compounds of Formula (I) when, for example, hydrogen is enriched in the deuterium isotope, the symbol "D" is used to represent the enrichment in deuterium.

Particularly preferred compounds of Formula (I) are compounds of Formula (Ia), where $R^1$, $R^2$, $R^3$ and A are as defined for Formula (I):

Formula (Ia)

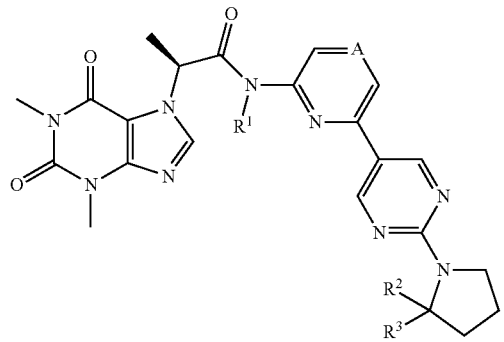

Compounds of Formula (I) include molecules having an aqueous solubility suitable for intravenous administration leading to or resulting in the treatment of pain symptoms and/or inhibition of the TRPA1 ion channel with a therapeutically effective potency. The potency of compounds of Formula (I) in inhibiting the TRPA1 ion channel was measured using the method of Example 1. FIG. 1 discloses the TRPA1 inhibition in vitro potency (measured by the method of Example 1). Preferred compounds of Formula (I) include compounds that inhibit the TRPA1 ion channel with a $IC_{50}$ value obtained by the method of Example 1 of less than about 100 nM (preferably, less than about 76 nM, more preferably less than about 25 nM) and most preferably less than or similar to the comparable measurement of Comparator Compound 2. Table 1 shows data obtained from the in vitro assay described in Example 1, where an "A" value represents an $IC_{50}$ value of less than 25 nano-molar (nM); a "B" value represents an $IC_{50}$ value between 25 and 75 nM; a "C" value represent an $IC_{50}$ value between 76 and 100 nM; and a "D" value represents an $IC_{50}$ value exceeding 100 nM.

Compounds of Formula (I) (preferably compounds of Formula (Ia)) where $R^1$ is H can inhibit the TRPA1 ion channel. Compounds of Formula (Ia) are preferably provided in compositions with more of a compound of Formula (Ia) than the corresponding stereoisomer(s) of Formula (Ib). For example, a pharmaceutical composition can contain a therapeutically effective amount of a compound of Formula (Ia) in an excess over the corresponding stereoisomers of Formula (Ib) (e.g., a compound of Formula (Ia) represents more than at least about 50% and preferably 78%, 85%, 90%, 95% or more of the total amount of compounds of Formula (I) in a composition). Compounds of Formula (I) (preferably compounds of Formula (Ia)) where $R^1$ is —$CH_2$—$R^{1a}$, and $R^{1a}$ is a phosphate moiety can be administered as part of an intravenous pharmaceutical composition to treat pain in therapeutically effective manner. Upon intravenous administration, compounds of Formula (I) (preferably compounds of Formula (Ia)) where $R^1$ is —$CH_2$—$R^{1a}$, and $R^{1a}$ is a phosphate moiety can be converted in vivo into compounds of Formula (I) that therapeutically inhibit the TRPA1 ion channel (e.g., where $R^1$ is H).

FIG. 1 also discloses the aqueous solubility measured at various pH values (using the method of Example 2) for various compounds of Formula (I) and certain comparator compounds. Unless otherwise indicated herein, the aqueous solubility of certain compounds of Formula (I) was measured using the method of Example 2. Preferred compounds of Formula (I) include compounds having an aqueous solubility of greater than about 0.1 mg/mL (preferably, greater than about 1 mg/mL) at a therapeutically relevant pH (e.g., about pH 2-7, and preferably about pH 7 for intravenous administration), as measured by the method of Example 2. In addition, the data in FIG. 1 show compounds of Formula (Ia) where $R^1$ is —$CH_2$—$R^{1a}$, and $R^{1a}$ is a phosphate moiety have improved aqueous solubility compared to Comparator Compound 2 as measured by the method of Example 2 (e.g., less than 1 mg/mL, preferably less than about 0.1 mg/mL).

Referring to FIG. 1, compositions comprising compounds of Formula (Ia) where $R^1$ is H have improved potency in inhibiting the TRPA1 ion channel using the method of Example 1, compared to comparator compounds 2-10 (e.g., less than 1 mg/mL, preferably less than about 0.1 mg/mL). Specific compounds of Formula (I) include molecules where A is CH, $R^1$ is hydrogen or —$CH_2$—$R^{1a}$ ($R^{1a}$ being a phosphate moiety), $R^3$ is $CF_3$, and $R^2$ is H, including compounds shown in Table 1b. Additional compounds of Formula (I) include molecules where A is N, $R^1$ is hydrogen or —$CH_2$—$R^{1a}$ ($R^{1a}$ being a phosphate moiety), $R^3$ is $CF_3$, and $R^2$ is H, including compounds shown in Table 1c. Compounds of Formula (I) also include molecules where A is N, $R^1$ is hydrogen or —$CH_2$—$R^{1a}$ ($R^{1a}$ being a phosphate moiety), $R^2$ is $CH_3$, and $R^3$ is $CH_3$, including compounds shown in Table 1d. Compounds of Formula (I) where A is N, $R^1$ is hydrogen or —$CH_2$—$R^{1a}$ ($R^{1a}$ being a phosphate moiety), $R^3$ is $CH_3$, and $R^2$ is H include compounds shown in Table 1e. Additional compounds of Formula (I) are molecules where A is CH, $R^1$ is hydrogen or —$CH_2$—$R^{1a}$ ($R^{1a}$ being a phosphate moiety), $R^3$ is $CH_3$, and $R^2$ is H, including compounds shown in Table 1f.

Figure 2A:
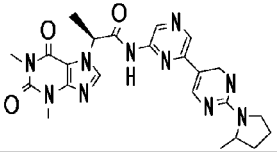
FIG. 2A (Table 2) (as FIGS. 2A-1 to 2A-2) is a data table showing the results from testing compounds of Formula (I) in the rodent formalin pain model described in Example 3.

Compounds of Formula (Ia) were effective in treating pain, as evaluated by the methods of Example 3 (rodent formalin pain model) and Example 4 (rodent cold plate pain model). In FIG. 2A, Table 2 discloses data obtained by testing compounds of Formula (Ia) and a control (vehicle) administered without a compound of Formula (I) according to the method of Example 3. The rodent formalin-induced pain model data in Table 2 shows that compounds of Formula (Ia) reduced the duration of pain behavior observed for the control in the absence of a compound of Formula (I) (i.e., the duration of pain behavior was less than 88 minutes observed for the control). FIG. 2B is a graph showing the results obtained by testing a compound of Formula (Ia) (i.e., Compound 1-A, structure in Table 2, FIG. 2) and a vehicle (without a compound of Formula (I)) in a rodent cold plate pain model described in Example 4. The data shown in FIG. 2B shows increased rodent Paw Withdrawal Latency (PWL) observed after i.p. administration of pharmaceutical compositions of Compound 1-A in the Complete Freud's Adjuvant rodent model. This data was obtained by measuring the change in PWL score as a function of the concentration of Compound 1-A, as well as a control vehicle composition, as described in Example 4. The data in FIG. 2A shows that compounds of Formula (Ia) reduce the symptoms of pain as measured according to the method of Example 3, and that a compound of Formula (Ia) (Compound 1-A) has an analgesic effect on cold allodynia as measured according to the method of Example 4. FIG. 2C shows Cold Plate Model data obtained for Comparator Compound 15.

Compounds of Formula (Ia) shown in FIG. 3 (Table 3) and certain comparator compounds were evaluated in a rodent acute tolerability test described in Example 5, showing alteration in liver function tests (LFTs) were observed by measurements of alanine aminotranferease (ALT) and aspartate aminotranferease (AST). Unexpectedly, in contrast to the Comparator Compounds in Table 3, intravenous administration of the compounds of Formula (Ia) as indicated in Table 3 did not result in elevation of either ALT or AST levels in the blood. Results in Table 3 are provided as a percentage of the highest normal expected concentrations of ALT and AST in the tested animals (i.e., 40 mg/dL ALT and 90 mg/dL AST). The data in Table 3 shows that intravenous bolus dose of the Comparator Compounds 1, 3, 4, 5 and 6 all resulted in significant subsequent increases in blood levels of ALT and AST to levels more than double (i.e., about 170-1,311%) of the high end of the normal ranges of these compounds prior to administration of the compounds. Preferred compounds of Formula (I) result in an ALT and/or AST level measured by the method of Example 5 of less than about 100 mg/dL one day after administration.

Examples of compounds of Formula (I) when $R^1$ is —$CH_2$—$R^{1a}$ ($R^{1a}$ being a phosphate moiety) that did not result in abnormally high levels of LFT compounds ALT or AST as measured according to Example 5 include a compound selected from the group consisting of:

(S)-(2-(1,3-dimethyl-2,6-dioxo-1,2,3,6-tetrahydro-7H-purin-7-yl)-N-(6-(2-(2,2-dimethylpyrrolidin-1-yl)pyrimidin-5-yl)pyrazin-2-yl)propanamido)methyl dihydrogen phosphate;

((S)-2-(1,3-dimethyl-2,6-dioxo-1,2,3,6-tetrahydro-7H-purin-7-yl)-N-(6-(2-((S)-2-(trifluoromethyl)pyrrolidin-1-yl)pyrimidin-5-yl)pyridin-2-yl)propanamido)methyl dihydrogen phosphate;

((S)-2-(1,3-dimethyl-2,6-dioxo-1,2,3,6-tetrahydro-7H-purin-7-yl)-N-(6-(2-((S)-2-methylpyrrolidin-1-yl)pyrimidin-5-yl)pyrazin-2-yl)propanamido)methyl dihydrogen phosphate;

((S)-2-(1,3-dimethyl-2,6-dioxo-1,2,3,6-tetrahydro-7H-purin-7-yl)-N-(6-(2-((S)-2-(trifluoromethyl)pyrrolidin-1-yl)pyrimidin-5-yl)pyrazin-2-yl)propanamido)methyl dihydrogen phosphate; and pharmaceutically acceptable salts thereof.

These compounds can be converted within a mammal (e.g., within the blood) into a compound of Formula (I) where $R^1$ is hydrogen to form a structurally corresponding compound selected from the group consisting of:

(S)-2-(1,3-dimethyl-2,6-dioxo-1,2,3,6-tetrahydro-7H-purin-7-yl)-N-(6-(2-(2,2-dimethylpyrrolidin-1-yl)pyrimidin-5-yl)pyrazin-2-yl)propanamide;

(S)-2-(1,3-dimethyl-2,6-dioxo-1,2,3,6-tetrahydro-7H-purin-7-yl)-N-(6-(2-((S)-2-(trifluoromethyl)pyrrolidin-1-yl)pyrimidin-5-yl)pyridin-2-yl)propanamide;

(S)-2-(1,3-dimethyl-2,6-dioxo-1,2,3,6-tetrahydro-7H-purin-7-yl)-N-(6-(2-((S)-2-methylpyrrolidin-1-yl)pyrimidin-5-yl)pyrazin-2-yl)propanamide, (S)-2-(1,3-dimethyl-2,6-dioxo-1,2,3,6-tetrahydro-7H-purin-7-yl)-N-(6-(2-((S)-2-(trifluoromethyl)pyrrolidin-1-yl)pyrimidin-5-yl)pyrazin-2-yl)propanamide, and pharmaceutically acceptable salts thereof.

Compounds of Formula (I) may be synthesized in a variety of ways. The processes shown in FIGS. 4, 5A, 5B, and 6, as described in Examples 6 and 7, are exemplary methods for synthesizing compounds of Formula (I). The reactions can be performed in solvents appropriate to the reagents and materials employed and are suitable for the transformations being effected. Disclosed reaction conditions, including choice of solvent, reaction atmosphere, reaction temperature, duration of the experiment and workup procedures, are chosen to be the conditions suitable for each reaction, as recognized by one skilled in a relevant technology. As understood by one skilled in the art of organic synthesis, the functionality present on various portions of the molecule can be selected or modified from recited examples herein to be compatible with various reagents and reactions to obtain other desired products. Such restrictions to the substituents, which are compatible with the reaction conditions, will be readily apparent to one skilled in the art and alternate methods must then be used.

Figure 4:
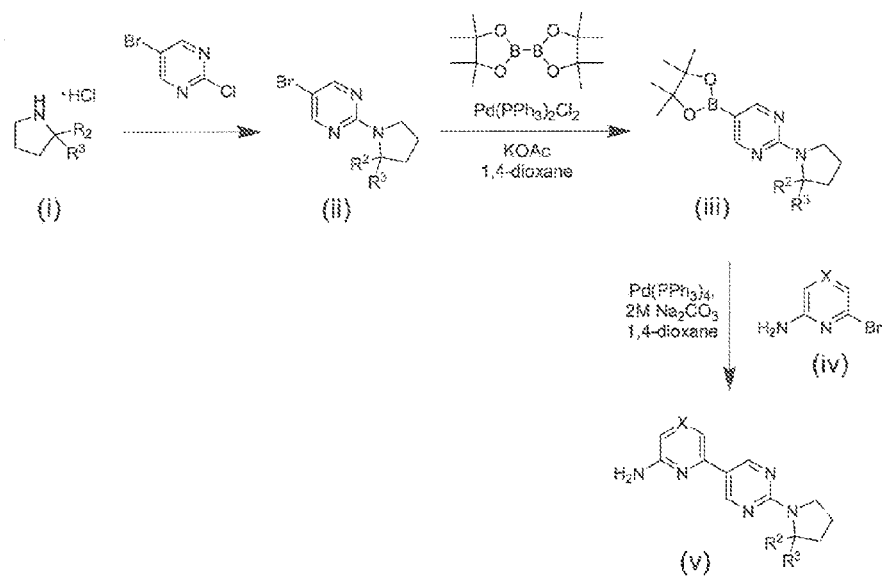
FIG. 4 depicts a general synthesis for intermediates useful in the synthesis of compounds of Formula (I).

Referring to FIG. 4, intermediates useful for the synthesis of compounds of Formula (I) can be formed by: (1) reacting an alpha mono- or di-alkyl substituted pyrrolidine (i) with 5-bromo-2-chloropyrimidine to form compound (II), (2) reacting compound (II) with bis(pinacolato)diboron in the presence of a suitable catalyst (e.g., palladium) to form compound (iii), and (3) coupling compound (iii) with compound (iv) in the presence of a suitable (e.g., palladium) catalyst to form intermediate (v) (where X can be N or CH).

Figure 5A:
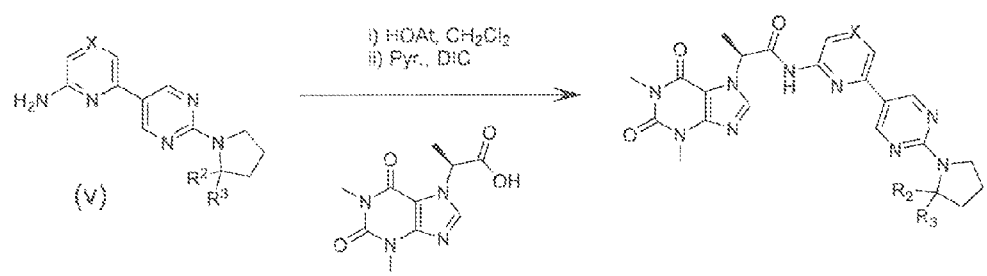
FIG. 5A depicts a general synthesis for compounds of Formula (I), wherein $R^1$ is hydrogen.

FIG. 5A provides a reaction scheme for synthesizing a compound of Formula (I) when $R^1$ is hydrogen, using compound (v) as starting material (X being N or CH). As further described in the Examples, compound (v) can be coupled with (S)-2-(1,3-dimethyl-2,6-dioxo-1,2,3,6-tetrahydro-7H-purin-7-yl)propanoic acid under appropriate conditions and in the presence of reagents such as DIC or triphenylphosphine and DIPEA at room temperature.

Figure 5B:
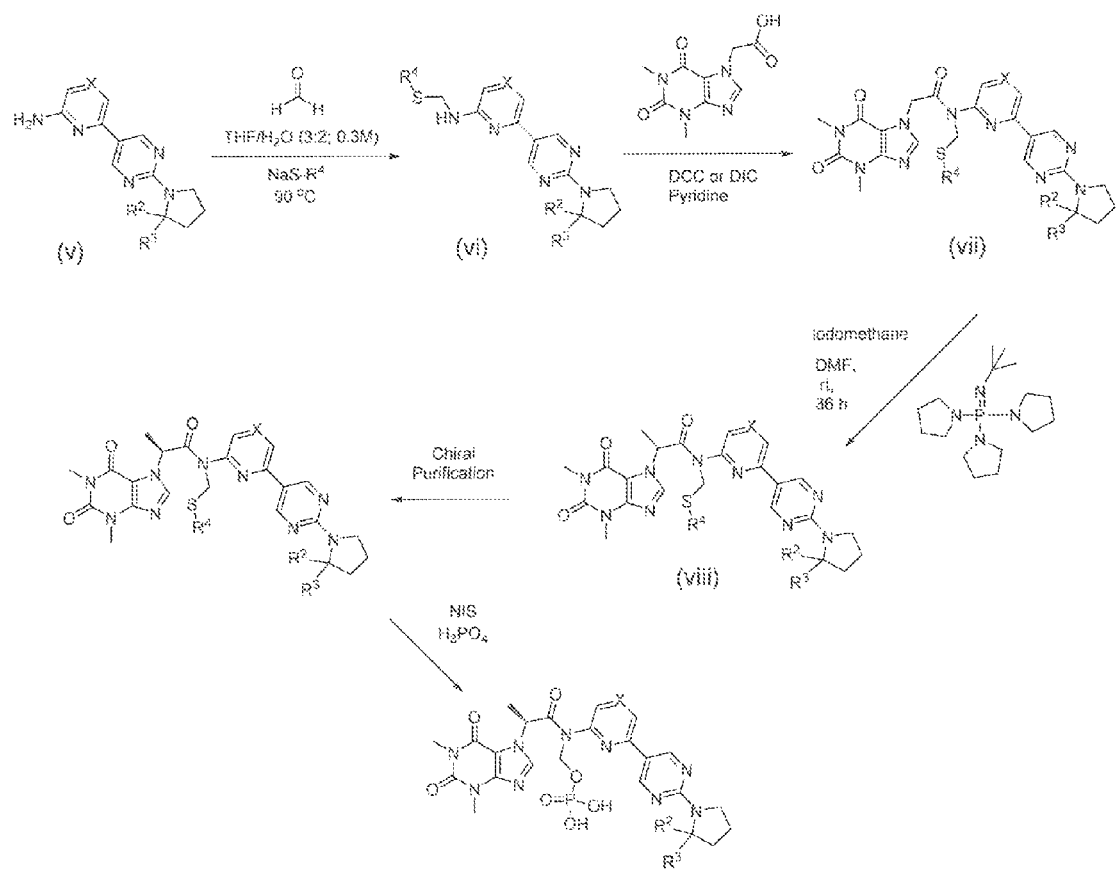
FIG. 5B depicts a general synthesis for compounds of Formula (I), wherein $R^1$ is $CH_2$-phosphate.

FIG. 5B is a synthetic route for synthesizing compounds of Formula (I) when $R^1$ is —$CH_2$—$R^{1a}$, where $R^{1a}$ is a phosphate moiety. The route can include: (1) thioesterification of the compound (v) with NaS—$R^4$ (wherein $R^4$ is $C_{1-4}$alkyl) to form compound (vi), (2) coupling compound (vi) with 2-(1,3-dimethyl-2,6-dioxo-1,2,3,6-tetrahydro-7H-purin-7-yl) acetic acid to form compound (vii), (3) methylating compound (vii) with a suitable methylating agent such as iodomethane to form compound (viii), and (4) formation of the pro-drug by one or more reactions to form the compound of Formula (I). Compound (viii) can be chirally purified before or after conversion to the of Formula (I) when $R^1$ is —$CH_2$—$R^{1a}$, where $R^{1a}$ is a phosphate moiety.

The compounds of Formula (Ia) are also useful in the manufacture of a pharmaceutical composition formulated for intravenous administration to treat pain (e.g., a prodrug compound of Formula (Ia) where $R^1$ is —$CH_2$—$R^{1a}$, and $R^{1a}$ is a phosphate moiety that can be converted to another compound of Formula (Ia) where $R^1$ is H in vivo after administration). A pharmaceutical composition formulated for intravenous administration for the treatment of pain can include a therapeutically effective amount of compound of Formula (Ia) shown in FIG. 1 where $R^1$ is —$CH_2$—$R^{1a}$ ($R^{1a}$ being a phosphate moiety). The amount of the compound (Ia) and indicated method of administration of the pharmaceutical composition can be selected to provide to a subject in need thereof a therapeutically effective amount of a compound of formula (Ia) where $R^1$ is hydrogen within the subject after administration of the pharmaceutical composition (e.g., by in vivo conversion of the compound of Formula (Ia) where $R^1$ is —$CH_2$—$R^{1a}$ ($R^{1a}$ being a phosphate moiety) to a therapeutically effective amount of compound of Formula (Ia) where $R^1$ is hydrogen within the body of the subject). For example, a pharmaceutical composition comprising Compound 1-A, 5-S, 2-E or 3-J can have an aqueous solubility suitable for intravenous administration. Upon intravenous administration to a subject in need thereof, the Compound 1-A, 5-S, 2-E or 3-J can be converted to a corresponding stereoisomer 1-B, 5-T, 2-F or 3-K effective for treatment of pain (e.g., by inhibiting the TRPA1 ion channel with a therapeutically effective potency).

Pharmaceutical compositions containing compounds of Formula (I) or pharmaceutically acceptable salts thereof can be used to treat or ameliorate medical conditions responsive to the inhibition of the TRPA1 ion channel in subjects (e.g., humans and animals). For example, the pharmaceutical compositions comprising compounds of Formula (I), or pharmaceutically acceptable salts thereof, are useful as a perioperative analgesic, for example in the management of mild to moderate acute post-operative pain and management of moderate to severe acute pain as an adjunct to opioid analgesics. The pharmaceutical compositions comprising a therapeutically-effective dose of compounds of Formula (I), can be administered to a patient for treatment of pain in a clinically safe and effective manner, including one or more separate administrations of the pharmaceutical compositions comprising compounds of Formula (I). For example, a pharmaceutical composition comprising a therapeutically effective dose of compounds of Formula (I), or pharmaceutically acceptable salts thereof can be administered (e.g., intravenously) to a subject in need thereof multiple times per day (e.g., BID) over a course of treatment of one or more days to treat pain in the subject.

Pharmaceutical compositions containing compounds of Formula (I) (e.g., Formula (Ia)) or pharmaceutically acceptable salts thereof can also be used to treat or ameliorate respiratory conditions, such as obstructive diseases, e.g., chronic obstructive pulmonary disease (COPD), asthma (e.g., Cold induced asthma, exercise-induced asthma, allergy-induced asthma, and occupational asthma), and cough.

The amount and concentration of compounds of Formula (I) in the pharmaceutical compositions, as well as the quantity of the pharmaceutical composition administered to a subject, can be selected based on clinically relevant factors, such as medically relevant characteristics of the subject (e.g., age, weight, gender, other medical conditions, and the like), the solubility of compounds in the pharmaceutical compositions, the potency and activity of the compounds, and the manner of administration of the pharmaceutical compositions. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

EXAMPLES

Example 1

Method for Measuring Inhibition of the TRPA1 Ion Channel

Compounds of Formula (I) inhibit the TRPA1 channel, as measured using the method of Example 1. Unless otherwise indicated, the method of Example 1 was used to measure in vitro inhibition of human TRPA1 provided in data tables shown in FIG. 1, using the procedure outlined in del Camino et al., *The Journal of Neuroscience*, 30(45):15165-15174 (Nov. 10, 2010), incorporated herein by reference and summarized below. Data for TRPA1 inhibition and for TRPA1 selectivity was obtained by this method for the indicated compounds of Formula (I), with the relevant data included in Table 1 below. All currents were recorded in whole-cell configuration using EPC-9 and EPC-10 amplifiers and Patchmaster software (HEKA). Patch pipettes had a resistance of 1.5-3 MΩ and 60-75% of the series resistance was compensated. The standard pipette solution consisted of 140 mM CsAsp, 10 mM EGTA, 10 mM HEPES, 2.27 mM $MgCl_2$, 1.91 mM $CaCl_2$, 4 mM MgATP, and 0.1-0.3 mM $Na_2GTP$, with pH adjusted to 7.2 with CsOH. In addition, a solution containing 145 mM CsCl, 10 mM HEPES, 10 mM EGTA and 1 mM $MgCl_2$ (pH 7.2 adjusted with CsOH) can be used. The standard bath solution contained 150 mM NaCl, 10 mM HEPES, 10 mM glucose, 4.5 mM KCl, 1 mM EGTA, 3 mM $MgCl_2$, with pH adjusted to 7.4 with NaOH. In some instances, 2 mM $CaCl_2$ was added in place of EGTA and the concentration of $MgCl_2$ was reduced to 1 mM.

Data were collected either by continuous recordings at −60 mV or by applying voltage ramps from a holding potential of 0 mV every 4 s. Continuous recordings were collected at 400 Hz and digitally filtered off-line at 10 Hz for presentation. Voltage ramps were applied from −100 mV to 100 mV over the course of 400 ms, and data were collected at 10 kHz and filtered at 2.9 kHz. Inward and outward currents were analyzed from the ramps at −80 and 80 mV, respectively. Liquid junction potential correction was not used.

Solutions were switched using a gravity-fed continuous focal perfusion system. To achieve rapid temperature changes, two temperature control, and perfusion systems were employed simultaneously. For temperatures≥22° C., a Warner Instruments bipolar temperature controller (TC-344B) and inline heater (SHM-8) were used. For temperatures below 22° C. a Warner Instruments temperature controller (CL-100) and thermal cooling module (TCM-1) were used. Temperatures were confirmed using a thermistor (Warner Instruments, TA-29), with temperatures at the recorded cell estimated to be within +/−2° C. of those reported.

Referring to FIG. 1, Tables 1a-1f show data obtained from the in vitro assay described in Example 1, where an "A" value represents an IC50 value of less than 25 nM; a "B" value represents an IC50 value between 25 and 75 nM; a "C" value represent an IC50 value between 76 and 100 nM; and a "D" value represents an IC50 value exceeding 100 nm. The antagonist effects of compounds of Formula (I) against human TRPA1 ("hTRPA1") and for some compounds rat TRPA1 ("rTRPA1") in a whole cell patch configuration were evaluated using the in vitro assay described above. The current activation tested was 10 µM AITC, and the tested concentrations ranged from 5 micromolar and 500 nanomolar.

Example 2

Method for Measuring Aqueous Solubility

Compounds of Formula (I) where $R^1$ is —$CH_2$—$R^{1a}$, and $R^{1a}$ is phosphate, have suitable levels of aqueous solubility for incorporation in a pharmaceutical composition formulated for intravenous administration. Unless otherwise indicated, the aqueous solubility of compounds of Formula (I) in Tables in FIG. 1 was measured using the procedure of Example 2 (Kerns, E. H., Journal of Pharmaceutical Sciences 2001, 90, 1838-1858, incorporated herein by reference). Solubility data was obtained by this method for compounds of Formula (I) and included in FIG. 1. The chromatographic data was performed using (type of HPLC). The column used was an Xbridge Shield RP18 with the following column dimensions: 4.6×30 mm, 3.5 µm. The mobile phase consisted of deionized water (MPA) with trifluoroacetic acid added in at 0.1% (v/v) (MPC) and HPLC-grade acetonitrile (MPB). The mobile phase flow rate was 2.5 mL/min with the column and sampling operating at ambient temperature. UV detection was set to 280 nm. For all samples used for solubility determination, the mobile phase gradient used was as follows in Table 1g below.

TABLE 1g

| Time (min) | % MPA | % MPB | % MPC |
|---|---|---|---|
| 0.00 | 70 | 20 | 10 |
| 1.08 | 0 | 90 | 10 |
| 1.20 | 0 | 90 | 10 |
| 1.21 | 70 | 20 | 10 |
| 1.50 | 70 | 20 | 10 |

Stock solutions of compounds of Formula (I) where $R^1$ is —$CH_2$—$R^{1a}$, and $R^{1a}$ is phosphate, were prepared in water at 20 mg/mL. Stock solutions of the compounds of Formula (I), wherein $R^1$ is hydrogen, were prepared in dimethyl acetamide at 20 mg/mL. All stock solutions of the compounds of Formula (Ia) were soluble at 20 mg/mL at ambient temperature.

Samples for analysis of the compounds of Formula (Ia) were prepared at a % v/v=1/19 (i.e., 10 µL of the stock solution into 190 µL of buffer) by spiking stock solutions of the compounds of Formula (Ia) into buffered solutions. Three buffered solution systems were prepared: pH 4.0 prepared from 50 mM sodium acetate in a 5% dextrose in water solution, pH 7.4 prepared from 75 mM sodium phosphate in a 1:1 ratio of sterilized water for injection to a 5% dextrose in water solution, and pH 9.0 prepared from 50 mM sodium bicarbonate in a 1:2 ratio of sterilized water for injection to a 5% dextrose in water solution.

The samples were incubated on a microplate shaker at 300 rpm for 24 hours at ambient temperature. Following incubation, the samples were centrifuged for five minutes at 13 k rpm at ambient temperature. The resulting supernatant was extracted for HPLC analysis.

Example 3

Rodent Formalin Pain Model

Compounds of Formula (I) are active in rodent models of pain induced by direct activation of the TRPA1 channel with intraplantar injection of the TRPA1 agonist formalin. Compounds of Formula (I) were tested in the formalin-induced pain test reported by Abbott et. al. Pain. 1995 January; 60(1): 91-102 (incorporated herein by reference in its entirety). Dubuisson et al. describe a method for assessing pain and analgesia in rats. Briefly, dilute formalin (50 µL of 3% formalin) is injected into the plantar surface of the hind paw. The animal is promptly returned to an observation arena (standard Plexiglass rat cage), at which point a trained observer records the time the animal spends exhibiting pain behaviors (flinching, licking, biting of the injected paw/leg) for a period of 5 minutes (split out as the first 2 minutes and the total time period of five minutes). The individual responsible for counting the pain behaviors in a particular study is blinded to the treatment groups.

Figure 2:
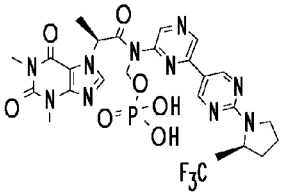
FIG. 2B is a line graph demonstrating increased Paw Withdrawal Latency scores observed after i.p. administration of pharmaceutical compositions with increasing concentrations of a compound of Formula (I) in the Complete Freund's Adjuvant rodent model of Example 4.
FIG. 2C is a line graph demonstrating Paw Withdrawal Latency scores for Comparator Compound 2.
Figure 2B:
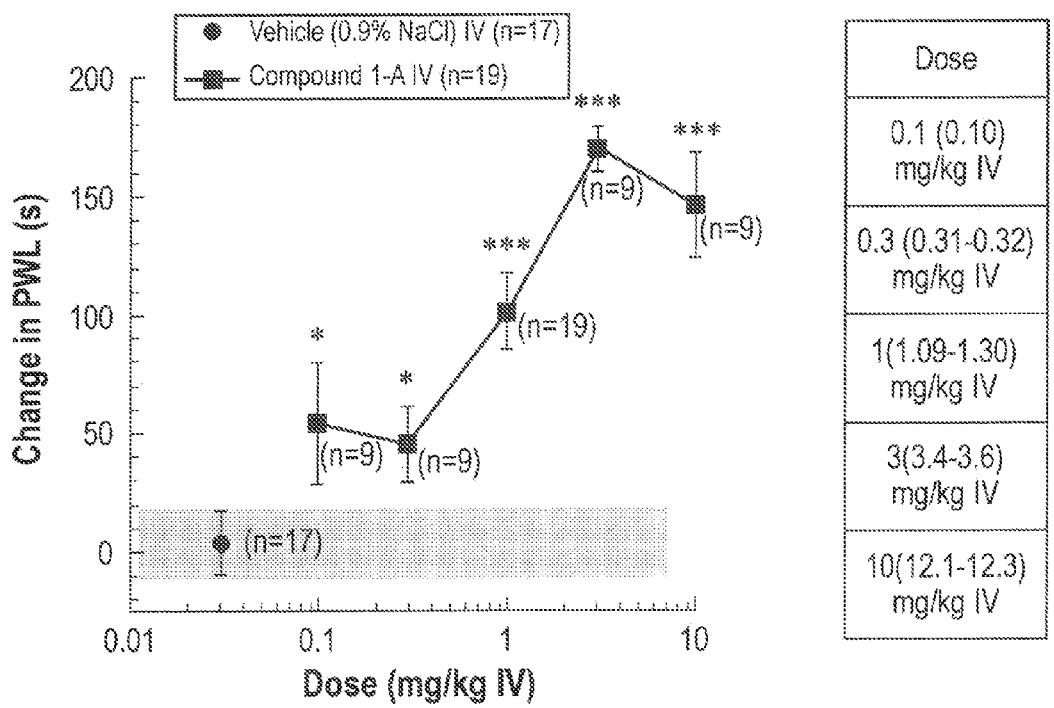
Figure 2C:
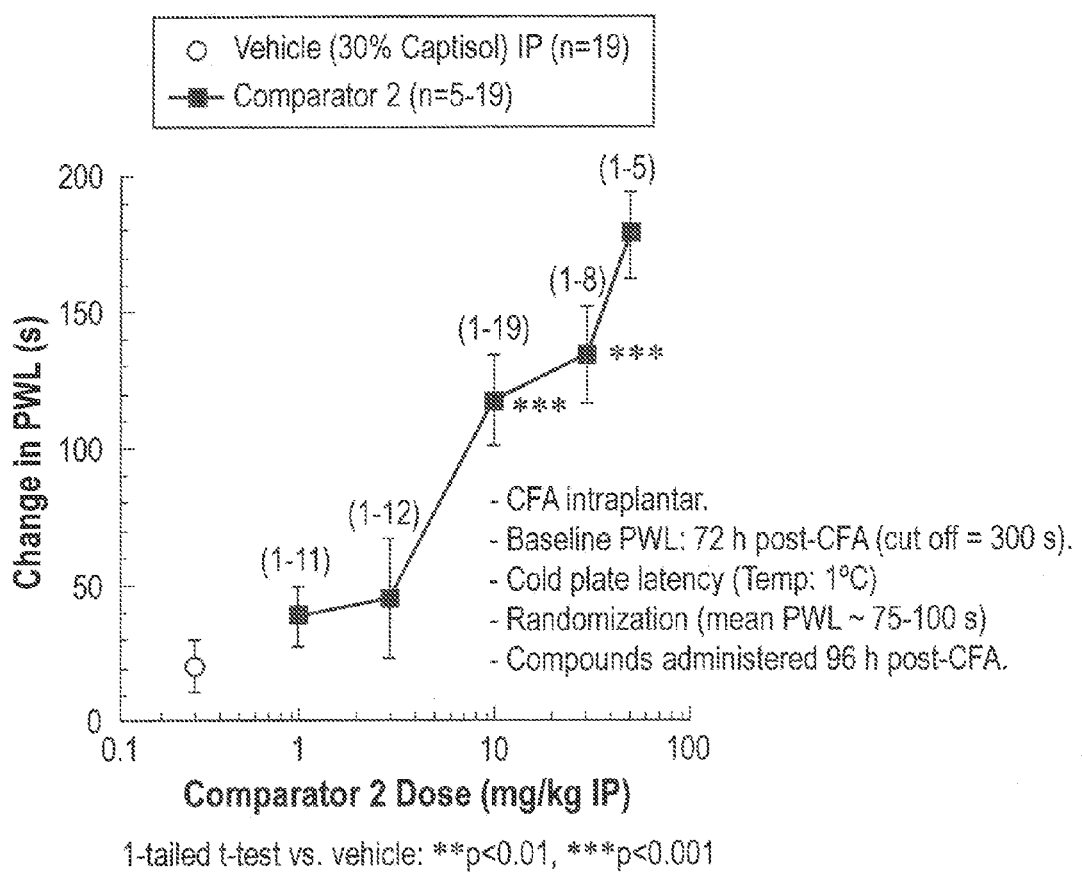

FIG. 2 (Table 2) is a data table showing the results from testing compounds of Formula (I) in the rodent formalin-induced pain model described in Example 2. Rats were treated with the compounds of Formula (I) at various doses (0.1, 0.3, 1, 1.2, 3, 4, 10, or 30 mg/kg IV) or with a control composition containing the vehicle (i.e., without a compound of Formula (I)). Pain behaviors (flinch, lift, lick, bite) were monitored following intraplantar formalin injection. Results from the first two minutes are shown in Table 2. Referring to Table 2, the minimum effective dose was derived from dose resulting in statistically significant difference in behavior at 0-2 min time period as compared with vehicle (p=<0.05).

Example 4

Rodent Cold Plate Pain Model

The efficacy of compound of Formula (I) in treating pain was further demonstrated by the Complete Freund's Adjuvent (CFA) model of inflammatory pain in the rat. CFA-induced pain test method reported in del Camino et al., J. Neurosci., 30 (45):15165-15174, incorporated herein by reference in its entirety. Briefly, the right hind paw is sensitized to cold temperature (allodynic) by administering 0.1 mL of Complete Freund's Adjuvant (CFA) to that paw. Two to four days later, the time it takes for the animal to lift its CFA-injected paw from the cold surface is recorded compared to its un-injected normal left hind paw. Animals are placed on the surface of the cold plate (1° C.) and the operator stops testing and notes the amount of time elapsed from first being placed on the plate to the instant the animal displays discomfort by flinching or lifting its paw from the plate (paw withdrawal latency, or PWL). To avoid tissue damage, the maximum cut-off time is five minutes. Animals that are allodynic (average PWL to the first three pain behaviors<150 seconds for the CFA-injected hind paw: ~≥50% difference between the normal and CFA-injected paw) are included in the study and subsequently randomized across treatment groups. The following day, the animals in some groups are dosed with a test compound under blinded conditions. Following the one to two hour pre-treatment time, the post-dose PWL readings are taken again. The efficacy of the drug treatment is assessed by comparing the PWL in the drug treatment animals to those that receive the vehicle. The data obtained are shown in FIG. 2B for tests using Compound 1-A, showing the reversal of CFA Cold Allodynia. In comparison, prior art Comparator Compound (sodium salt administered as 0.5% methyl cellulose suspension) showed efficacy at 150 mg/kg in the CFA cold plate model of inflammatory pain in the rat.

Example 5

Rodent Acute Tolerability Test

Compounds of Formula (I) were assessed for acute tolerability in a rodent model at dose levels ranging from 100-200 mg/kg based upon the minimum efficacious dose of each compound. Female Sprague Dawley rats were administered up to a 10 mL/kg dose volume of each compound in 0.9% saline at appropriate concentrations as an intravenous bolus via the lateral tail vein. The animals were observed immediately post dose and for up to twenty four hours post dose and clinical observations were recorded. Additionally, approximately twenty four hours post dose animals were euthanized and blood taken for serum chemistry analysis with a focus on liver function tests (LFTs). The maximum tolerated single dose and LFT results are summarized in Table 3 in FIG. 3, where (↔) indicates blood levels of markers for potential liver damage within normal range and (↑) indicates blood levels of markers for potential liver damage elevated above normal range. Referring to the data in Table 3, LFT blood levels of markers for potential liver damage remained within normal range for the compounds of Formula (I), while LFTs were elevated for Comparator Compounds including 5-10 fold elevation above normal for ALT and AST blood levels observed upon administration of Comparator Compound 1. Compounds of Formula (I) in Table 3 unexpectedly showed normal blood levels of the LFTs for ALT and AST in contrast to the elevated ALT and AST blood levels observed after about 24 hours after administration of the Comparator Compounds in Table 3.

Example 6

Synthesis of Intermediate Compounds

One or ordinary skill in the relevant technology can make compounds of Formula (I) based on the disclosure herein, including Example 7 and the Figures, using one or more intermediates disclosed and characterized in Example 6.

Example 6A

Intermediate 1, (S)-5-Bromo-2-(2-(trifluoromethyl)pyrrolidin-1-yl)pyrimidine

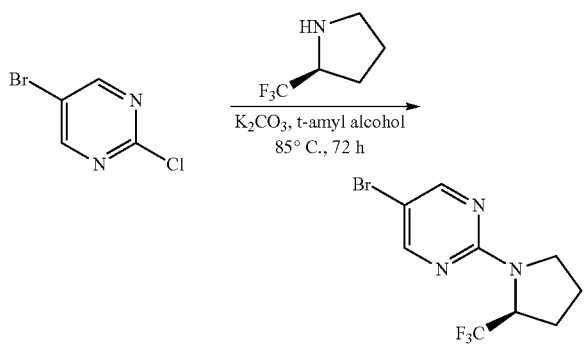

A flask was charged with 5-bromo-2-chloropyrimidine (36.62 g, 189 mmol), (S)-2-(trifluoromethyl)pyrrolidine (34.2 g, 246 mmol), potassium carbonate (39.2 g, 284 mmol)) and t-amyl alcohol (189 mL). The reaction mixture was stirred at 85° C. for 72 hours. The reaction mixture was then filtered over Celite®, washed with $CH_2Cl_2$ (2×) and concentrated in vacuo. The crude residue was redissolved in $CH_2Cl_2$ and washed with water and brine. The combined organic layers were dried over $MgSO_4$, filtered and concentrated in vacuo to give crystalline solids. The solids were washed with cold water (3×) and triturated with toluene to give the title product as pale orange crystals, 43.4 g (147 mmol, 77%); $^1$H NMR (300 MHz, DMSO-d6) δ 8.58 (s, 2H), 5.06-4.83 (m, 1H), 3.71-3.44 (m, 2H), 2.30-1.89 (m, 4H); m/z found $[M+H]^+$=295.99.

Example 6B

Intermediate 2, (S)-5-(4,4,5,5-tetramethyl-1,3,2-dioxaborolan-2-yl)-2-(2-(trifluoromethyl)pyrrolidin-1-yl)pyrimidine

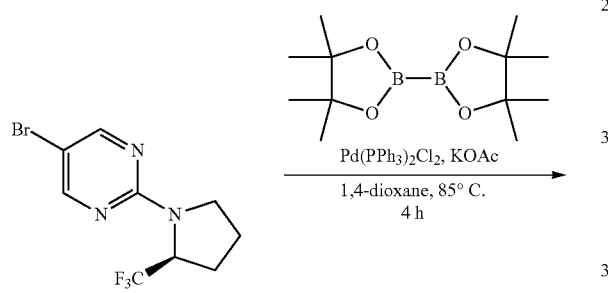

A dry flask was charged with compound (S)-5-bromo-2-(2-(trifluoromethyl)pyrrolidin-1-yl)pyrimidine (Intermediate 1, 43.4 g, 147 mmol), bis(pinacolato)diboron (44.7 g, 176 mmol), potassium acetate (28.8 g, 293 mmol) and bis(triphenylphosphine)palladium(II) chloride (10.29 g, 14.66 mmol). The flask was capped and purged with nitrogen (3×). The solids were suspended in anhydrous 1,4-dioxane (489 ml), stirred at 25° C. for 5 minutes and degassed with nitrogen for 15 minutes before stirring at 85° C. for 4 hours. The solvent was removed in vacuo. The resulting dark brown residue was suspended in water and extracted with $CH_2Cl_2$: MeOH 9:1 (3×). The combined organic layers were dried over $MgSO_4$, filtered and concentrated in vacuo. The crude material was purified on silica gel chromatography eluting with EtOAc:Hex (30:70) to yield 39.9 g (116 mmol, 79%) of the title product as white to yellow flaky solids; $^1$H NMR (300 MHz, DMSO-d6) δ 8.56 (s, 2H), 5.24-4.93 (m, 1H), 3.78-3.48 (m, 2H), 2.30-1.90 (m, 4H), 1.29 (s, 12H); m/z found $[M+H]^+$=261.07 (boronic acid)

Example 6C

Intermediate 3, (S)-6-(2-(2-(trifluoromethyl)pyrrolidin-1-yl)pyrimidin-5-yl)pyridine-2-amine

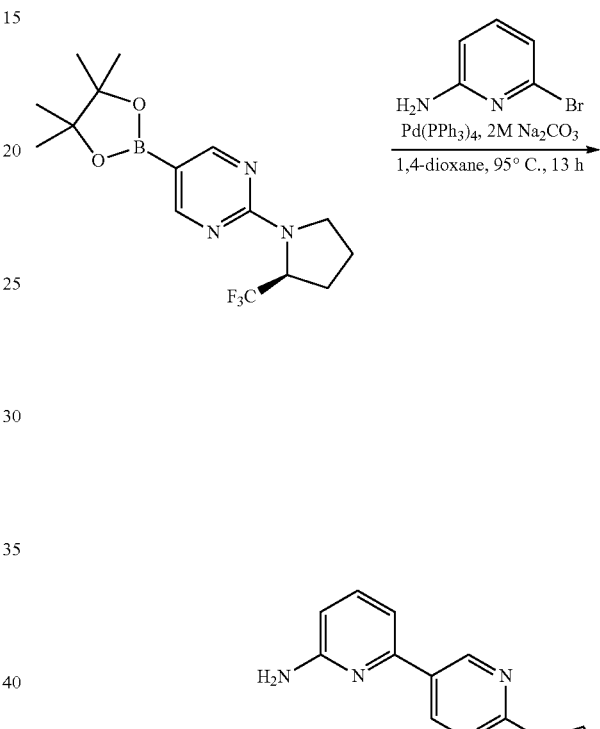

A flask was charged with (S)-5-(4,4,5,5-tetramethyl-1,3,2-dioxaborolan-2-yl)-2-(2-(trifluoromethyl)pyrrolidin-1-yl) pyrimidine (Intermediate 2, 5 g, 14.57 mmol), 6-bromopyridin-2-amine (3.03 g, 17.48 mmol), $Pd(PPh_3)_4$ (1.684 g, 1.457 mmol) and 1,4-dioxane (36 mL). The reaction mixture was purged with nitrogen for several minutes before aqueous 2M sodium carbonate (14.57 mL, 29.1 mmol) solution was added. The reaction mixture was then purged with nitrogen for another 10 minutes at 25° C. before it was heated to 90° C. under nitrogen overnight. 1,4-Dioxane was removed in vacuo and the crude mixture was diluted with EtOAc. The product was washed with water (3×) and brine. The combined organic layers were dried over $MgSO_4$, filtered and concentrated under reduced pressure. The crude material was purified on silica gel chromatography eluting with MeOH:$CH_2Cl_2$ (2:98) to yield 3.75 g (12.13 mmol, 83%) of the title product as an off white solid; $^1$H NMR (300 MHz, DMSO-d6) δ 8.99 (s, 2H), 7.44 (dd, J=8.1, 7.5 Hz, 1H), 7.13-6.93 (m, 1H), 6.47-6.34 (m, 1H), 6.04 (s, 2H), 5.22-4.90 (m, 1H), 3.67 (t, J=6.1 Hz, 2H), 2.32-1.95 (m, 4H); m/z found [M+H]⁺=310.45.

Example 6D

Intermediate 4, (S)—N-((methylthio)methyl)-6-(2-(2-(trifluoromethyl)pyrrolidin-1-yl)pyrimidin-5-yl)pyridine-2-amine

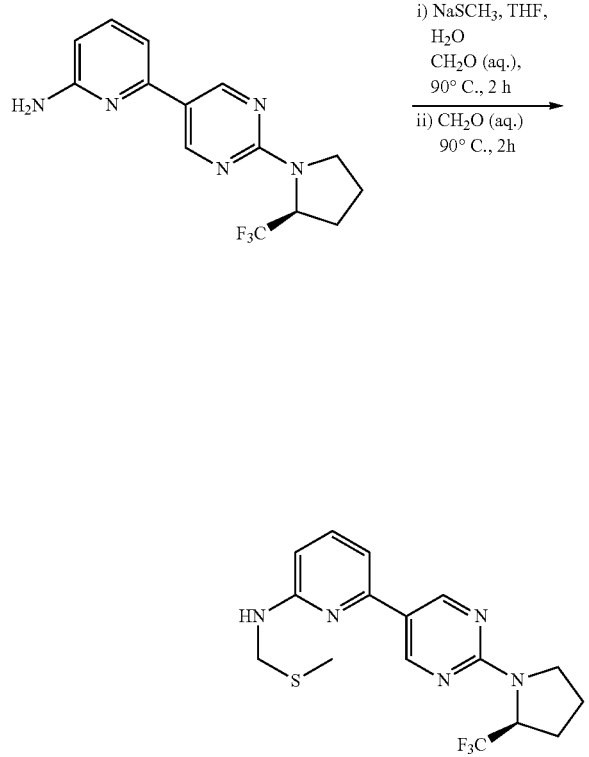

A 350 mL pressure vessel was charged with (S)-6-(2-(2-(trifluoromethyl)pyrrolidin-1-yl)pyrimidin-5-yl)pyridine-2-amine (Intermediate 3, 10 g, 32.3 mmol) and sodium methanethiolate (4.53 g, 64.7 mmol), which were dissolved in a mixture of THF (64.7 mL) and water (43.1 mL). Aqueous 37% formaldehyde (5.25 mL, 64.7 mmol) was added and the reaction mixture was heated to 90° C. for 2 hours. Another 2 eq. of aqueous 37% formaldehyde were added and the reaction mixture was heated for an additional 2 hours. The reaction mixture was then cooled to 25° C. The layers were separated in the separatory funnel and the aqueous layer was extracted with EtOAc (3×). The combined organic layers were washed with brine, dried over MgSO₄, filtered and concentrated in vacuo. The crude material was purified using silica gel chromatography, eluting with EtOAc:Hex (30:70) to yield 9 g (24.36 mmol, 75%) of the title product as an oil; ¹H NMR (300 MHz, DMSO-d6) δ 9.07 (s, 2H), 7.56-7.43 (m, 1H), 7.41 (t, J=6.6 Hz, 1H), 7.13 (d, J=7.3 Hz, 1H), 6.51 (d, J=8.2 Hz, 1H), 5.18-4.98 (m, 1H), 4.59 (d, J=6.7 Hz, 2H), 3.69 (dd, J=10.3, 4.9 Hz, 2H), 2.21-2.0 (m, 4H), 2.12 (s, 3H); m/z found [M+H]⁺=370.35.

Example 6E

Intermediate 5, (S)-2-(1,3-dimethyl-2,6-dioxo-1,2,3,6-tetrahydro-7H-purin-7-yl)-N-((methylthio)methyl)-N-(6 (2 (2 (trifluoromethyl)pyrrolidin-1-yl)pyrimidin-5-yl)pyridin-2-yl)acetamide

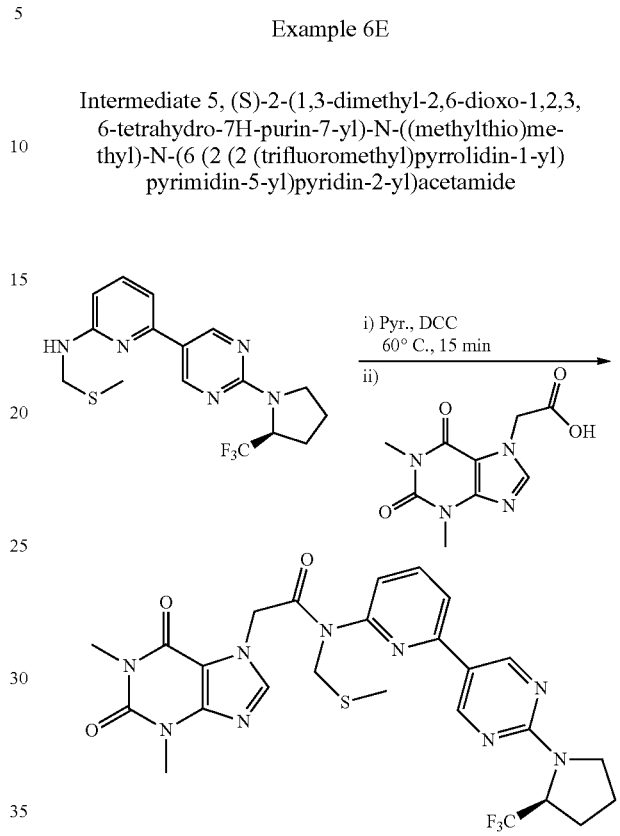

A solution of (S)—N-((methylthio)methyl)-6-(2-(2-(trifluoromethyl)pyrrolidin-1-yl)pyrimidin-5-yl)pyridine-2-amine (Intermediate 4.17 g, 46.0 mmol) and DCC (18.99 g, 92 mmol) in pyridine (230 mL) was heated for 30 minutes at 60° C. before theophylline 7-acetic acid (21.92 g, 92 mmol) was added in one portion. The reaction mixture was stirred at 60° C. and monitored by LCMS. After 2 hours, additional theophylline 7-acetic acid (21.92 g, 92 mmol) and DCC (18.99 g, 92 mmol) were added to drive the reaction to completion. The reaction mixture was diluted with CH₂Cl₂. The resulting precipitate (DCC urea) was filtered over Celite® and washed with CH₂Cl₂ (3×). The mixture was diluted with water and adjusted to pH 3 with aqueous 3M HCl. The organic and aqueous layers were separated and the aqueous layer was extracted with additional CH₂Cl₂ (3×). The combined organic layers were washed with aqueous 1M HCl (2×), dried over MgSO₄, filtered and concentrated in vacuo. The crude material was purified using silica gel chromatography, eluting with EtOAc:Hex (70:30) to yield 18.5 g (31.4 mmol, 68%) of the title product as a thick oil; ¹H NMR (300 MHz, DMSO-d6) δ 9.21 (s, 2H), 8.16-8.03 (m, 2H), 7.99 (d, J=7.6 Hz, 1H), 7.60 (d, J=7.7 Hz, 1H), 5.33 (s, 2H), 5.12 (m, 3H), 3.82-3.65 (m, 2H), 3.43 (s, 3H), 3.18 (s, 3H), 2.31-2.09 (m, 4H), 2.06 (s, 3H); m/z found [M+H]⁺=590.37.

Alternatively, the coupling of (S)—N-((methylthio)methyl)-6-(2-(2-(trifluoromethyl)pyrrolidin-1-yl)pyrimidin-5-yl)pyridine-2-amine and theophylline 7-acetic acid may be facilitated with propanephosphonic anhydride and DIPEA in acetonitrile at room temperature.

Example 6F

Intermediate 6, (S)-2-(1,3-dimethyl-2,6-dioxo-1,2,3,6-tetrahydro-7H-purin-7-yl)-N-((methylthio(methyl)-N-(6-(2-((S)-2-(trifluoromethyl)pyrrolidin-1-yl)pyrimidin-5-yl)pyridin-2-yl)propanamide

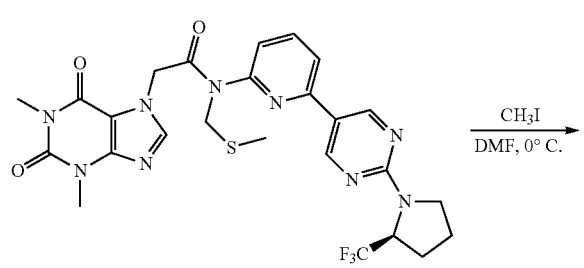

A solution of (S)-2-(1,3-dimethyl-2,6-dioxo-1,2,3,6-tetrahydro-7H-purin-7-yl)-N-((methylthio)methyl)-N-(6-(2-(2-(trifluoromethyl)pyrrolidin-1-yl)pyrimidin-5-yl)pyridin-2-yl)acetamide (Intermediate 5, 6.2 g, 10.52 mmol) in DMF (52.6 mL) was charged with iodomethane (1.312 mL, 21.03 mmol). The reaction mixture was cooled to 0° C. and 2-methyl-N-(tri(pyrrolidin-1-yl)phosphoranylidene)propan-2-amine (6.44 mL, 21.03 mmol) was added dropwise. The reaction mixture was stirred for 30 minutes. An additional 2 eq of iodomethane (1.312 mL, 21.03 mmol) and 2 eq of phosphazene base (6.44 mL, 21.03 mmol) were added to drive the reaction to completion. The reaction mixture was cooled to 0° C. and the pH was adjusted to 4-5 with aqueous 1M HCl. The reaction mixture was diluted with water and extracted with EtOAc (3×). The combined organic layers were dried over MgSO₄, filtered and concentrated in vacuo. The crude mixture of diastereomers material was purified via silica gel chromatography, eluting with MeOH:CH₂Cl₂ (2:98) to yield 14.2 g (23.52 mmol, 75%) the title product as a yellow solid. A mixture of diastereomers was resolved using SFC purification to give the (S,S)-isomer in 6.21 g (retention time: 1.8 minutes, de: 98.5%) and the (R,S)-isomer in 6.72 g (retention time: 2.6 minutes, de: 96%); ¹H NMR, (S,S)-isomer: (300 MHz, DMSO-d6) δ 8.87 (s, 2H), 8.12 (s, 1H), 8.04 (t, J=7.8 Hz, 1H), 7.93 (d, J=7.5 Hz, 1H), 7.59 (d, J=7.6 Hz, 1H), 5.79-5.64 (m, 1H), 5.14 (d, J=13.9 Hz, 1H), 5.09-5.00 (m, 1H), 4.92 (d, J=13.9 Hz, 1H), 3.85-3.63 (m, 2H), 3.36 (s, 3H), 2.98 (s, 3H), 2.34-2.07 (m, 4H), 2.03 (s, 3H), 1.58 (d, J=6.9 Hz, 3H); m/z found [M+H]⁺=604.49.

Example 6G

Intermediate 7, Methyl(S)-2-(1,3-dimethyl-2,6-dioxo-1,2,3,6-tetrahydro-7H-purin-7-yl)propanoate

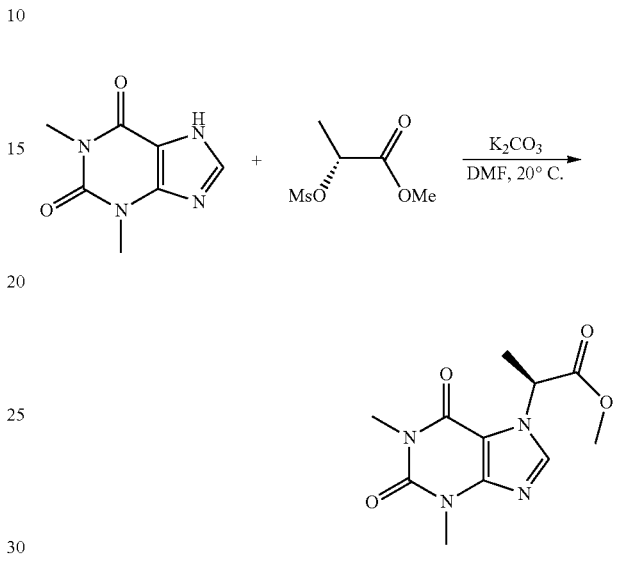

To a suspension of 1,3-dimethyl-1H-purine-2,6(3H,7H)-dione (20 g, 111 mmol) and K₂CO₃ (30.6 g, 222 mmol) in DMF (400 mL) was added (R)-methyl 2-((methylsulfonyl)oxy)propanoate (which may be synthesized according to the procedure described in PCT Pub No. WO/2005/059107 (40 g, 222 mmol). The reaction mixture was stirred at 20° C. for 20 h. The reaction mixture was then quenched with saturated NH₄Cl(aq), diluted with water and extracted with CH₂Cl₂ (3×). The combined organic extracts were washed 3× with 10% LiCl (aq), dried over Na₂SO₄ and evaporated in vacuo. The residue was purified using silica gel column chromatography eluting first with PE:CH₂Cl₂ (1:1) followed by CH₂Cl₂:MeOH (50:1) to give 13.5 g (50.7 mmol, 45.7%, ee: 95%) of the (S)-product. The (S)-product was analyzed by chiral HPLC to determine it is at least 95% pure as the S-isomer (≥95% ee).

Example 6H

Intermediate 8, (S)-2-(1,3-Dimethyl-2,6-dioxo-1,2,3,6-tetrahydro-7H-purin-7-yl)propanoic acid

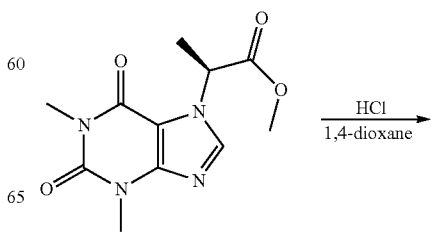

-continued

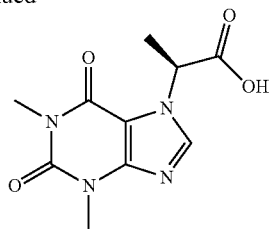

To a solution of methyl(S)-2-(1,3-dimethyl-2,6-dioxo-1,2,3,6-tetrahydro-7H-purin-7-yl)propanoate (Intermediate 7, 39 g, 146 mmol) in 1,4-dioxane (400 mL) was added 6N HCl (200 mL). The resulting mixture was refluxed for 3 h, then cooled and concentrated under vacuum (water bath temp: 40-45° C.). Water (35 mL) was added to the residue, and the resulting mixture was then stirred for 0.5 h. The precipitate was collected by filtration, washed with cooled water and ethyl acetate to give the (S)-acid (17.3 g, ee: 99%). The filtrate was carefully neutralized with $K_2HPO_4$ solution (aq) to pH 4, extracted with (9:1) $CH_2Cl_2$:MeOH mixture (2×), dried over $MgSO_4$, filtered, and concentrated. The residue was purified using silica gel chromatography eluting with $CH_2Cl_2$:MeOH (9:1) to give additional (S)-acid (3.2 g, ee: 95%).

Example 6I

Intermediate 9,2-(1,3-Dimethyl-2,6-dioxo-1,2,3,6-tetrahydro-7H-purin-7-yl)-N-(6-(2-(2,2-dimethylpyrrolidin-1-yl)pyrimidin-5-yl)pyrazin-2-yl)-N-((methylthio)methyl)acetamide

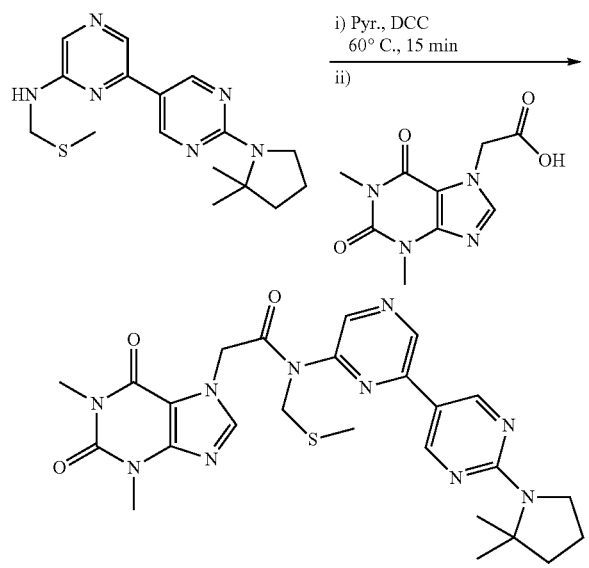

The title product was prepared from 6-(2-(2,2-dimethylpyrrolidin-1-yl)pyrimidin-5-yl)-N-((methylthio)methyl)pyrazin-2-amine (20.0 g, 60.5 mmol) using a procedure analogous to the one described for the synthesis of Intermediate 5. Yield: 21 g (33.9 mmol, 56%); $^1$H NMR (300 MHz, DMSO-d6) δ 9.17 (s, 1H), 9.14 (s, 2H), 8.82 (s, 1H), 8.08 (s, 1H), 5.41 (s, 2H), 5.19 (s, 2H), 3.68 (t, J=6.5 Hz, 2H), 3.43 (s, 3H), 3.19 (s, 3H), 2.08 (s, 3H), 1.91 (dt, J=12.2, 5.8 Hz, 4H), 1.54 (s, 6H); m/z [M+H]$^+$=551.64.

Example 7

Synthesis of Compounds of Formula (I) Using Intermediates from Example 6

Figure 6:
FIG. 6 depicts a general procedure for preparing HCl salts for compounds of Formula (I) wherein $R^1$ is hydrogen.

The following examples illustrate the synthesis of a composition comprising compounds of Formula (I), and pharmaceutically acceptable salts thereof. Further, the disclosure includes variations of the methods described herein to produce compounds of Formula (I) that would be understood by one skilled in the art. FIG. 4 is a general synthesis for intermediates useful in the synthesis of compounds of Formula (I), where X is N or CH. FIG. 5A is a general synthesis for compounds of Formula (I), wherein $R^1$ is hydrogen and X is N or CH. FIG. 5B is a general synthesis for compounds of Formula (I), wherein $R^1$ is $CH_2$-phosphate. In FIG. 5B, X can be N or CH, $R^2$ can be H or $CH_3$, $R^3$ can be $CH_3$ or $CF_3$ and $R^4$ is as disclosed herein. FIG. 6 depicts a general procedure for preparing HCl salts for compounds of Formula (I) wherein $R^1$ is hydrogen. In FIG. 6, X can be N or CH, $R^2$ can be H or $CH_3$, while $R^3$ can be $CH_3$ or $CF_3$.

Example 7A synthesis of ((S)-2-(1,3-dimethyl-2,6-dioxo-1,2,3,6-tetrahydro-7H-purin-7-yl)-N-(6-(2-((S)-2-(trifluoromethyl)pyrrolidin-1-yl)pyridine-2-yl)propanamido)methyl dihydrogen phosphate, sodium salt

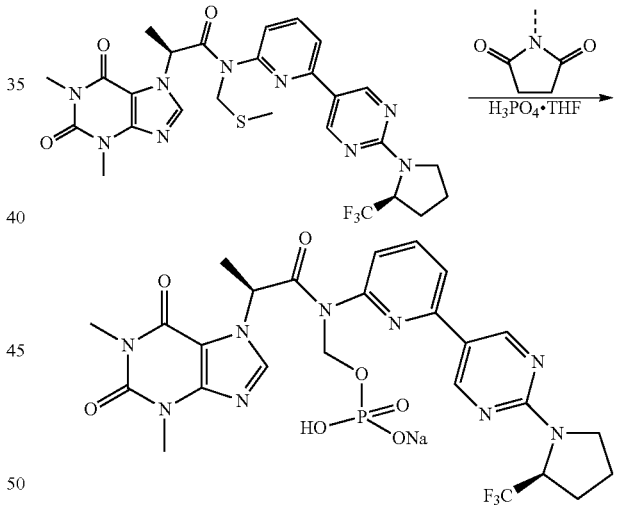

A dry flask was charged with (S)-2-(1,3-dimethyl-2,6-dioxo-1,2,3,6-tetrahydro-7H-purin-7-yl)-N-((methylthio(methyl)-N-(6-(2-((S)-2-(trifluoromethyl)pyrrolidin-1-yl)pyrimidin-5-yl)pyridin-2-yl)propanamide (Intermediate 6, 2.08 g, 3.45 mmol, de: 98.5%)) and 3A° activated molecular sieves (0.050 g). The flask was purged with nitrogen before crystalline phosphoric acid (9.79 g, 100 mmol) and anhydrous THF (17.23 mL) were added. The reaction mixture was stirred for 5 min at 25° C. before N-iodosuccinimide (NIS) (1.551 g, 6.89 mmol) was added in one portion. The reaction mixture was diluted with methanol and filtered over Celite®. The filtrate was cooled to 0° C. and quenched with saturated aqueous sodium thiosulfate followed by slow addition of aqueous NaOH (2 M), in 3 portions, to adjust to pH 7. The organic solvent was removed in vacuo at 25° C. and the aqueous solution was desalted over a Waters XBridge® C$_{18}$ column and eluted with 60% acetonitrile. The lyophilized powder was then purified by prep-HPLC over a Waters XBridge® C$_{18}$ column and eluted with 27% acetonitrile in 54 mM sodium phosphate buffer (pH 7.0). After removal of the organic solvent in vacuo, the desired fraction was further desalted and lyophilized to obtain 1.5 g (2.30 mmol, 66%, de>95%) of the (S,S) product; $^1$H NMR (300 MHz, DMSO-d6) δ 8.87 (s, 2H), 8.23 (s, 1H), 7.93 (t, J=7.9 Hz, 1H), 7.82 (d, J=7.5 Hz, 1H), 7.57 (d, J=7.9 Hz, 1H), 6.00 (d, J=7.1 Hz, 1H), 5.59 (s, 1H), 5.41 (s, 1H), 5.14-4.98 (m, 1H), 3.79-3.61 (m, 2H), 3.40 (s, 3H), 2.98 (s, 3H), 2.33-1.99 (m, 4H), 1.67 (d, J=6.4 Hz, 3H); m/z found [M+H]$^+$=654.47. EA: C (40.07%), H (3.95%), N (16.65%), P (3.95%), Na (4.02%).

Example 7B

Synthesis of (S)-2-(1,3-Dimethyl-2,6-dioxo-1,2,3,6-tetrahydro-7H-purin-7-yl)-N-(6-(2-((S)-2-(trifluoromethyl)pyrrolidin-1-yl)pyrimidin-5-yl)pyridin-2-yl)propanamide

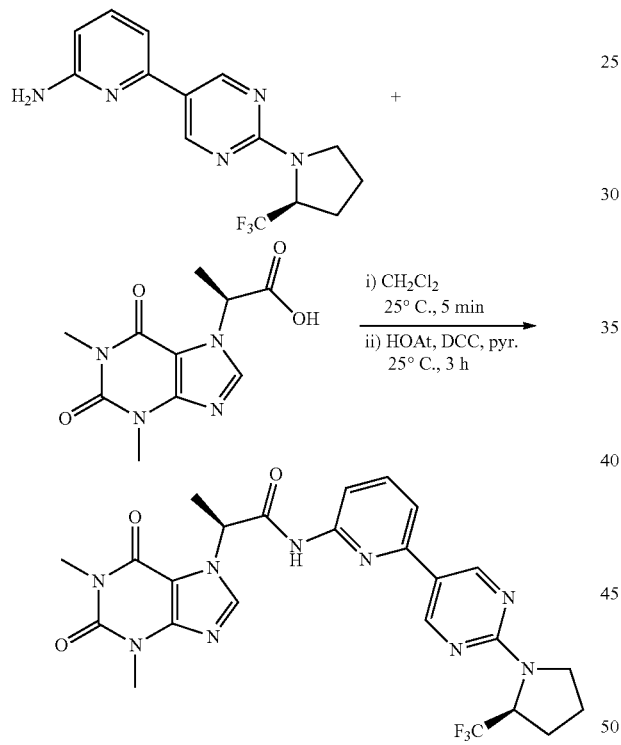

A flask was charged with (S)-6-(2-(2-(trifluoromethyl)pyrrolidin-1-yl)pyrimidin-5-yl)pyridine-2-amine (Intermediate 3, 5.44 g, 17.59 mmol) and (S)-2-(1,3-dimethyl-2,6-dioxo-1,2,3,6-tetrahydro-7H-purin-7-yl)propanoic acid (Intermediate 8, 5.10 g, 20.23 mmol, ee: 99%), CH$_2$Cl$_2$ (58.6 mL) and the resulting mixture was stirred at 25° C. for 5 minutes. To the resulting yellow heterogeneous mixture was added HOAt (2.394 g, 17.59 mmol) and DCC (6.90 g, 33.4 mmol). The reaction mixture was cooled to 0° C. and pyridine (2.85 mL, 35.2 mmol) was added slowly around the edges of the flask. The reaction mixture was kept at 0° C. for 5 minutes before it was removed from the ice bath, and was then stirred at 25° C. for 3 hours. The reaction mixture was diluted with CH$_2$Cl$_2$ and filtered over Celite® to remove urea byproduct. The filtrate was then quickly concentrated to an oil, taken up in minimal CH$_2$Cl$_2$ and added dropwise to stirring hexanes to precipitate out crude (S,S)-product which was dried overnight. The product was recrystallized from CH$_2$Cl$_2$:MeOH (4:1) to obtain the title product (4.78 g, 8.79 mmol, 50%, de>99%); $^1$H NMR; $^1$H NMR (300 MHz, DMSO-d6) δ 11.05 (s, 1H), 9.12 (s, 2H), 8.34 (s, 1H), 7.88 (dt, J=15.7, 8.1 Hz, 2H), 7.68 (d, J=8.2 Hz, 1H), 5.84 (d, J=6.7 Hz, 1H), 5.11 (p, J=7.4, 7.0 Hz, 1H), 3.83-3.61 (m, 2H), 3.46 (s, 3H), 3.19 (s, 3H), 2.33-1.96 (m, 4H), 1.87 (d, J=7.3 Hz, 3H); m/z [M+H]$^+$=544.20.

The hydrochloride salt of Example 7B may be prepared according to the procedure shown below:

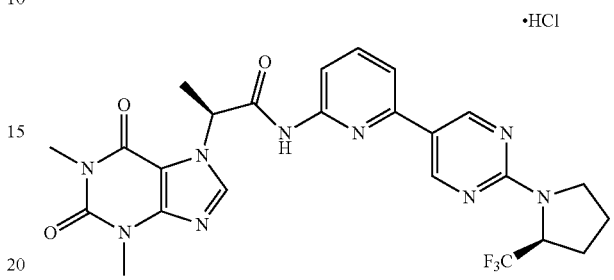

To a 1 L round bottom flask charged with dry (S)-2-(1,3-dimethyl-2,6-dioxo-1,2,3,6-tetrahydro-7H-purin-7-yl)-N-(6-(2-((S)-2-(trifluoromethyl)pyrrolidin-1-yl)pyrimidin-5-yl)pyridin-2-yl)propanamide (Example 2, 20.5 g, 43.1 mmol) was added 200 mL 4M HCl in dioxane. The resulting mixture was stirred at room temperature for 1 hr, during which time the reaction mixture change from a suspension, to a mostly homogenous clear yellow solution, to a white solid suspension in light yellow solvent. After 1 hr, the solids were collected via vacuum filtration with EtOH. The solids were rinsed with EtOH (3×100 mL) and placed under a high vacuum overnight. After 18 hr the material was removed from the high vacuum and transferred to an amber jar, providing the title product 22.6 g (>100%) as an off-white solid. (I) salt (m/z=M+=475), $^1$H NMR (300 MHz, DMSO-d6) δ 11.06 (s, 1H), 9.12 (s, 2H), 8.34 (s, 1H), 7.88 (dt, J=15.7, 8.2 Hz, 2H), 7.68 (d, J=8.4 Hz, 1H), 5.84 (d, J=7.0 Hz, 1H), 5.13 (q, J=8.1 Hz, 1H), 3.84-3.60 (m, 2H), 3.46 (s, 3H), 3.19 (s, 3H), 2.32-1.95 (m, 4H), 1.87 (d, J=7.3 Hz, 3H).

Example 8

Synthesis of (S)-2-(1,3-dimethyl-2,6-dioxo-1,2,3,6-tetrahydro-7H-purin-7-yl)-N-(6-(2-((S)-2-(trifluoromethyl)pyrrolidin-1-yl)pyrimidin-5-yl)pyrazin-2-yl)propanamide Example 8A Synthesis of (S)-5-Bromo-2-(2-(trifluoromethyl)pyrrolidin-1-yl)pyrimidine

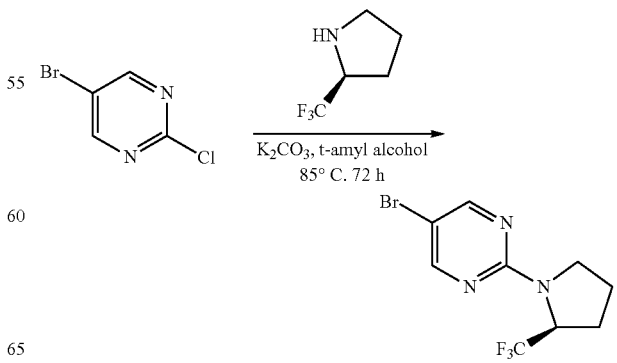

A flask was charged with 5-bromo-2-chloropyrimidine (36.62 g, 189 mmol), (S)-2-(trifluoromethyl)pyrrolidine (34.2 g, 246 mmol), potassium carbonate (39.2 g, 284 mmol)) and t-amyl alcohol (189 mL). The reaction mixture was stirred at 85° C. for 72 hours. The reaction mixture was then filtered over Celite®, washed with $CH_2Cl_2$ (2×) and concentrated in vacuo. The crude residue was redissolved in $CH_2Cl_2$ and washed with water and brine. The combined organic layers were dried over MgSO4, filtered and concentrated in vacuo to give crystalline solids. The solids were washed with cold water (3×) and triturated with toluene to give the title product as pale orange crystals, 43.4 g (147 mmol, 77%); $^1$H NMR (300 MHz, DMSO-d6)_8.58 (s, 2H), 5.06-4.83 (m, 1H), 3.71-3.44 (m, 2H), 10 2.30-1.89 (m, 4H); m/z found [M+H]+=295.99.

Example 8B

Synthesis of (S)-5-(4,4,5,5-tetramethyl-1,3,2-dioxaborolan-2-yl)-2-(2-(trifluoromethyl)pyrrolidin-1-yl)pyrimidine

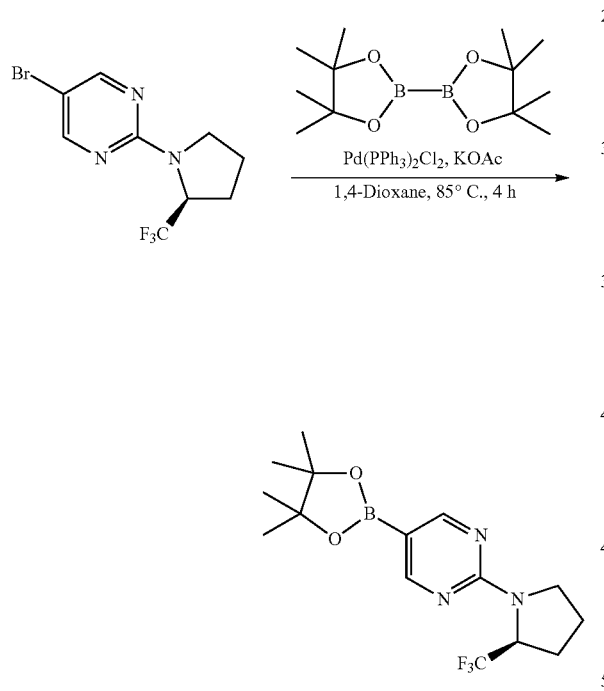

A dry flask was charged with compound (S)-5-bromo-2-(2-(trifluoromethyl)pyrrolidin-1-yl)pyrimidine (43.4 g, 147 mmol), bis(pinacolato)diboron (44.7 g, 176 mmol), potassium acetate (28.8 g, 293 mmol) and bis(triphenylphosphine) palladium(II) chloride (10.29 20 g, 14.66 mmol). The flask was capped and purged with nitrogen (3×). The solids were suspended in anhydrous 1,4-dioxane (489 ml), stirred at 25° C. for 5 minutes and degassed with nitrogen for 15 minutes before stirring at 85° C. for 4 hours. The solvent was removed in vacuo. The resulting dark brown residue was suspended in water and extracted with $CH_2Cl_2$:MeOH 9:1 (3×). The combined organic layers were dried over MgSO4, filtered and concentrated in vacuo. The crude material was purified on silica gel chromatography eluting with EtOAc:Hex (30:70) to yield 39.9 g (116 mmol, 79%) of the title product as white to yellow flaky solids; $^1$H NMR (300 MHz, DMSO-d6)_8.56 (s, 2H), 5.24-4.93 (m, 1H), 3.78-3.48 (m, 2H), 2.30-1.90 (m, 4H), 1.29 (s, 12H); m/z found [M+H]+=261.07 (boronic acid)

Example 8C

Synthesis of (S)-6-(2-(2-(trifluoromethyl)pyrrolidin-1-yl)pyrimidin-5-yl)pyrazin-2-amine

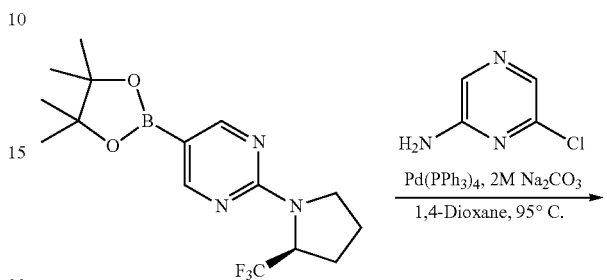

A round bottom flask was charged with 6-chloropyrazin-2-amine (0.401 g, 3.09 mmol), (S)-5-(4,4,5,5-tetramethyl-1,3,2-dioxaborolan-2-yl)-2-(2-(trifluoromethyl)pyrrolidin-1-yl)pyrimidine (1.062 g, 3.09 mmol), Pd(PPh3)4 (0.358 g, 0.309 mmol) and 1,4-Dioxane (Volume: 7.74 ml). The reaction mixture was purged with nitrogen for several minutes before an aqueous 2M sodium carbonate (3.09 ml, 6.19 mmol) was added. The reaction mixture was purged for another 10 minutes under nitrogen before it was placed in a 90° C. oil bath and allowed to stir overnight. 1,4-Dioxane was removed in vacuo and the crude mixture was diluted with EtOAc. The product was wash with water (3×) and brine. The combined organic layers were dried over MgSO4, filtered and concentrated under reduced pressure. The crude material was purified on silica gel using normal phase flash chromatography, eluting with $CH_2Cl_2$:MeOH to yield 0.655 g (2.11 mmol, 68.2%) of the title product; $^1$H NMR (300 MHz, DMSO-d6)

δ 9.01 (s, 2H), 8.26 (s, 1H), 7.83 (s, 1H), 6.55 (s, 2H), 5.16-5.02 (m, 1H), 3.77-3.60 (m, 2H), 2.29-2.01 (m, 4H); m/z [M+H]⁺=311.12

Example 8D

Synthesis of (S)-2-(1,3-dimethyl-2,6-dioxo-1,2,3,6-tetrahydro-7H-purin-7-yl)-N-(6-(2-((S)-2-(trifluoromethyl)pyrrolidin-1-yl)pyrimidin-5-yl)pyrazin-2-yl)propanamide

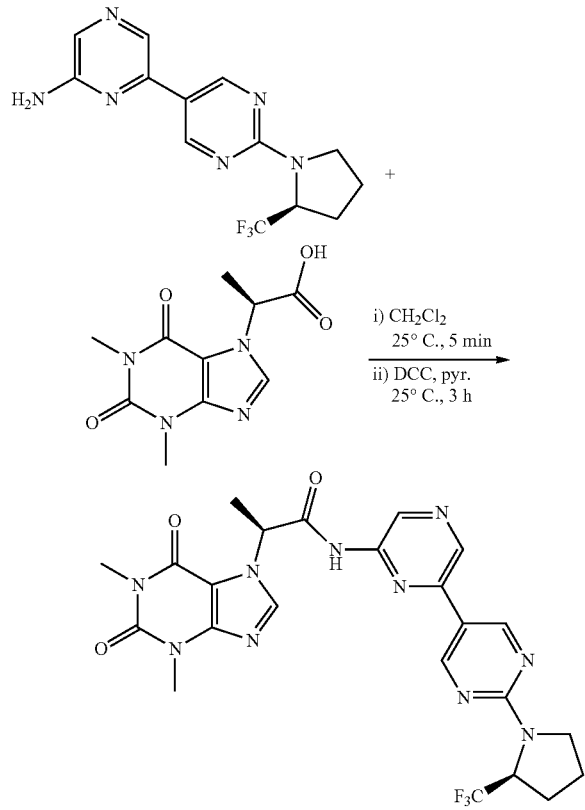

A round bottom flask was charged with (S)-6-(2-(2-(trifluoromethyl)pyrrolidin-1-yl)pyrimidin-5-yl)pyrazin-2-amine (5.097 g, 16.43 mmol) and (S)-2-(1,3-dimethyl-2,6-dioxo-2,3-dihydro-1H-purin-7(6H)-yl)propanoic acid (Intermediate 8) (4.97 g, 19.71 mmol). The reagents were suspended in DCM (Volume: 36.5 ml, Ratio: 4), sonicated and allowed to stir for 5 minutes. To the yellow heterogenous mixture was added DCC (5.76 g, 27.9 mmol) and finally pyridine (Volume: 18.25 ml, Ratio: 2) was added and the mixture was allowed to stir for 3 hours. The reaction mixture was diluted with CH₂Cl₂ and filtered over Celite®. The filtrate was then concentrated and redissolved in a minimal amount of and added dropwise to stirring hexanes to precipitate out crude 2-(1,3-dimethyl-2,6-dioxo-2,3-dihydro-1H-purin-7(6H)-yl)-N-(6-(2-((S)-2-(trifluoromethyl)pyrrolidin-1-yl)pyrimidin-5-yl)pyrazin-2-yl)propanamide, which was dried overnight. The mixture of diasteromers was resolved using SFC purification to give the (S,S)-isomer in 2.58 g (retention time: 2.5 min, de: 98%); and the (R,S)-isomer in 0.208 g (retention time: 2.2 min, de: 99%); ¹H NMR, (S,S)-isomer (300 MHz, DMSO-d6) δ 11.40 (s, 1H), 9.16 (d, J=3.5 Hz, 3H), 8.97 (s, 1H), 8.36 (s, 1H), 5.86 (d, J=7.3 Hz, 1H), 5.20-5.03 (m, 1H), 3.73 (t, J=6.5 Hz, 2H), 3.46 (s, 3H), 3.19 (s, 3H), 2.29-2.04 (m, 4H), 1.89 (d, J=7.3 Hz, 3H); m/z found [M+H]⁺=545.19

Example 9

Synthesis of (S)-2-(1,3-dimethyl-2,6-dioxo-1,2,3,6-tetrahydro-7H-purin-7-yl)-N-(6-(2-((S)-2-methylpyrrolidin-1-yl)pyrimidin-5-yl)pyrazin-2-yl)propanamide

Example 9A

Synthesis of (S)-5-bromo-2-(2-methylpyrrolidin-1-yl)pyrimidine

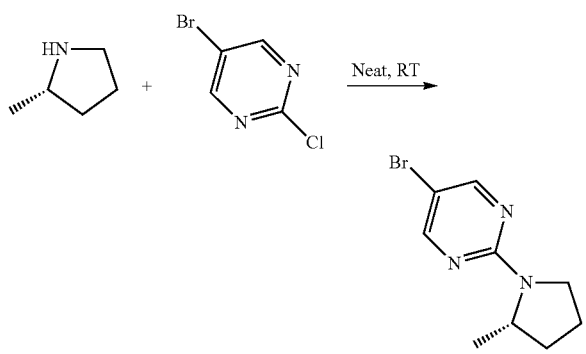

Solid 5-bromo-2-chloropyrimidine (27.5 g, 142 mmol) was added in three portions to a 500 mL flask containing (S)-2-methylpyrrolidine (20.24 ml, 213 mmol) stirred at room temperature. After 1 hr the resulting solids were dissolved in warm DCM, washed with water, brine, dried over MgSO₄ and concentrated onto silica in vacuo. Column purified by silica gel chromatography to afford white crystalline solids (30.7 g, 89%), ESI-MS (EI⁺, m/z): 241.02, ¹H NMR (Chloroform-d) δ: 8.31 (d, J=5.0 Hz, 2H), 4.33-4.14 (m, 1H), 3.61 (tt, J=7.6, 3.0 Hz, 1H), 3.56-3.41 (m, 1H), 2.23-1.88 (m, 3H), 1.88-1.63 (m, 1H), 1.25 (t, J=5.5 Hz, 3H)

Example 9B

Synthesis of (S)-2-(2-methylpyrrolidin-1-yl)-5-(4,4,5,5-tetramethyl-1,3,2-dioxaborolan-2-yl)pyrimidine

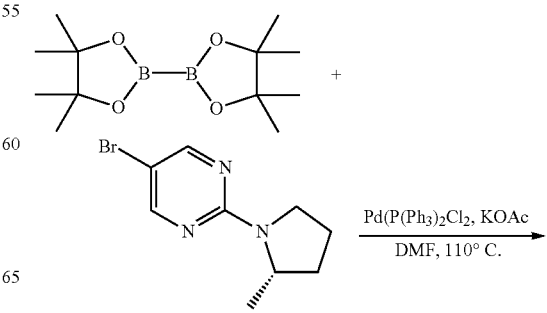

-continued

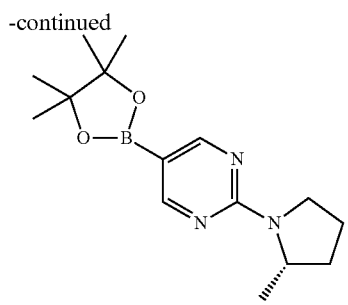

(S)-5-bromo-2-(2-methylpyrrolidin-1-yl)pyrimidine (18 g, 74.3 mmol), bis(pinacolato)diboron (28.3 g, 112 mmol), bis(triphenylphosphine)palladium chloride (10.44 g, 14.87 mmol) and potassium acetate (14.59 g, 149 mmol) were suspended in anhydrous dioxane (Volume: 372 ml). Nitrogen was bubbled through the solution for 15 minutes and then heated to reflux at 110° C. After 2 hours, the reaction mixture was cooled to room temperature and the solvents were removed in vacuo. To the resulting residue was added water and extracted with DCM. The combined organic layers were washed with brine, dried over MgSO$_4$ and concentrated in vacuo. Column purified by silica gel chromatography to afford yellow solids, (14.3 g, 66%) ESI-MS (EI$^+$, m/z): 289.2, $^1$H NMR (DMSO-d6) δ: 8.45 (s, 2H), 4.33-4.16 (m, 1H), 3.57 (ddd, J=10.4, 7.5, 2.8 Hz, 1H), 3.51-3.38 (m, 1H), 2.13-1.82 (m, 3H), 1.75-1.61 (m, 1H), 1.27 (s, 12H), 1.17 (d, J=6.3 Hz, 3H)

Example 9C

Synthesis of (S)-6-(2-(2-methylpyrrolidin-1-yl)pyrimidin-5-yl)pyrazin-2-amine

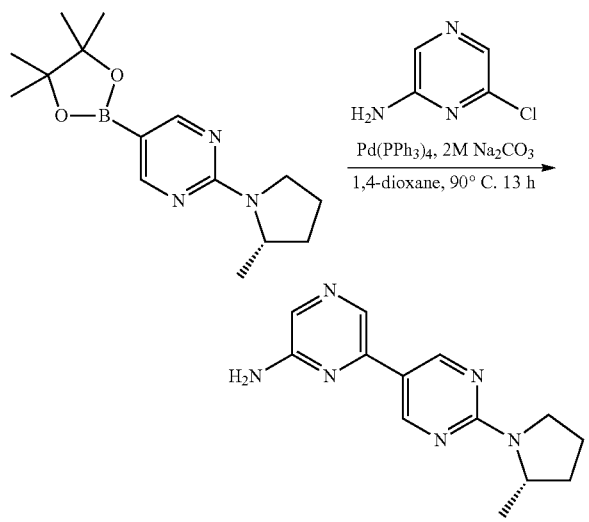

A flask was charged with (S)-2-(2-methylpyrrolidin-1-yl)-5-(4,4,5,5-tetramethyl-1,3,2-dioxaborolan-2-yl)pyrimidine (7.1 g, 24.55 mmol), 6-chloropyrazin-2-amine (2.89 g, 22.32 mmol), Pd(PPh$_3$)$_4$ (2.58 g, 2.232 mmol) and 1,4-dioxane (74.4 mL). The reaction mixture was purged with nitrogen for several minutes before aqueous 2M sodium carbonate (22.32 mL, 44.6 mmol) solution was added. The reaction mixture was then purged with nitrogen for another 10 minutes at 25° C. before it was heated to 90° C. under nitrogen overnight. 1,4-Dioxane was removed in vacuo and the crude mixture was diluted with EtOAc. The product was washed with water and brine. The combined organic layers were dried over MgSO$_4$, filtered and concentrated under reduced pressure. The crude material was purified on silica gel chromatography to yield 3.38 g (13.2 mmol, 84%) of the title product as a light brown solid. ESI-MS (EI$^+$, m/z): 258.26, $^1$H NMR (Chloroform-d) δ: 8.92 (d, J=5.3 Hz, 2H), 8.25 (s, 1H), 7.88 (s, 1H), 4.60 (s, 2H), 4.39 (d, J=5.8 Hz, 1H), 3.81-3.68 (m, 1H), 3.68-3.55 (m, 1H), 2.24-1.95 (m, 3H), 1.78 (s, 1H), 1.31 (d, J=6.3 Hz, 3H)

Example 9D

Synthesis of (S)-2-(1,3-dimethyl-2,6-dioxo-1,2,3,6-tetrahydro-7H-purin-7-yl)-N-(6-(2-((S)-2-methylpyrrolidin-1-yl)pyrimidin-5-yl)pyrazin-2-yl)propanamide

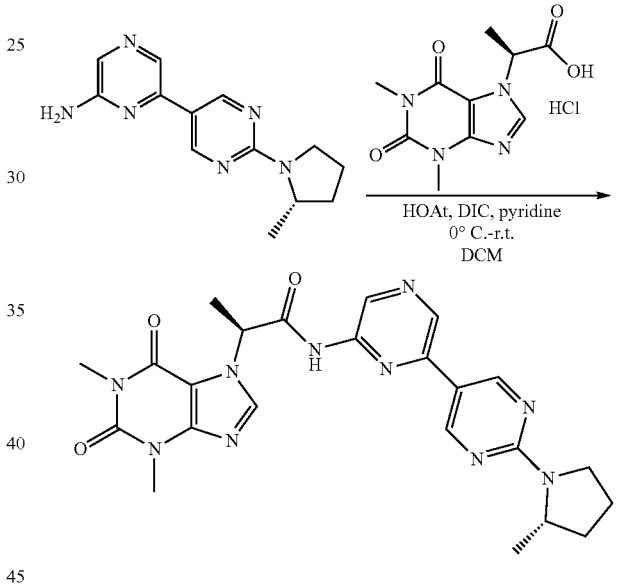

A flask was charged with (S)-2-(1,3-dimethyl-2,6-dioxo-2,3-dihydro-1H-purin-7(6H)-yl)propanoic acid hydrochloride (Intermediate 8) (8.96 g, 31.0 mmol), (S)-6-(2-(2-methylpyrrolidin-1-yl)pyrimidin-5-yl)pyrazin-2-amine (7.23 g, 28.2 mmol), HOAt (3.84 g, 28.2 mmol), nitrogen, DCM (141 ml) and stirred at room temperature. The suspension was cooled to 0° C. followed by addition of pyridine (4.60 ml, 56.4 mmol), then DIC (6.59 ml, 42.3 mmol). The reaction was removed from ice bath immediately after addition of DIC was complete. The reaction was complete after 7.5 hours. The reaction mixture was diluted with 100 mL DCM. The organic layer was washed with 0.5 M HCl aq. (2×20 mL). The resulting organic layer was washed with water, brine, dried over MgSO$_4$, filtered and concentrated. The resulting DCM filtrate was slowly added dropwise to 300 mL of stirred hexanes at room temperature. The resulting solids were collected via vacuum filtration with aide of hexanes and dried on on frit filter overnight to afford off-white solids (6.5 g, 13.25 mmol, 47.0% yield, 93% ee). ESI-MS (EI$^+$, m/z): 491.33, $^1$H NMR (DMSO-d6) δ: 11.35 (s, 1H), 9.10 (s, 1H), 9.05 (s, 2H), 8.91 (s, 1H), 8.36 (s, 1H), 5.85 (d, J=7.2 Hz, 1H), 4.30 (s, 1H), 3.59

(d, J=27.6 Hz, 2H), 3.46 (s, 3H), 3.19 (s, 3H), 2.08 (s, 3H), 1.95 (s, 1H), 1.88 (d, J=7.3 Hz, 3H), 1.72 (s, 1H), 1.24 (d, J=6.3 Hz, 3H)

Example 10

Synthesis of a Comparator Compound

Sodium (2-(1,3-dimethyl-2,6-dioxo-1,2,3,6-tetrahydro-7H-purin-7-yl)-N-(6-(2-(2,2-dimethylpyrrolidin-1-yl)pyrimidin-5-yl)pyrazin-2-yl)acetamido)methyl hydrogen phosphate

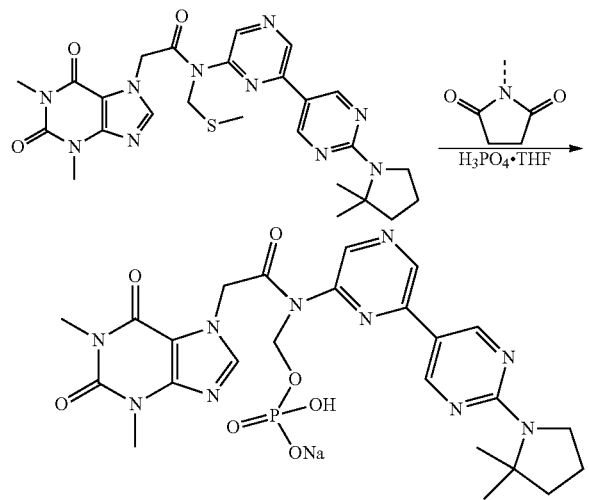

The title product was prepared from 2-(1,3-dimethyl-2,6-dioxo-1,2,3,6-tetrahydro-7H-purin-7-yl)-N-(6-(2-(2,2-dimethylpyrrolidin-1-yl)pyrimidin-5-yl)pyrazin-2-yl)-N-((methylthio)methyl)acetamide (Intermediate 9, 10.0 g, 10.1 mmol) using a procedure analogous to the one described for the synthesis of Example 1. Yield: 3.38 g (5.69 mmol, 31%); $^1$H NMR (300 MHz, Deuterium Oxide) δ 8.79 (s, 1H), 8.75 (s, 2H), 8.56 (s, 1H), 7.83 (s, 1H), 5.51 (d, J=7.0 Hz, 2H), 5.37 (br s, 2H), 3.54 (m, 2H), 3.32 (s, 3H), 3.14 (s, 2H), 1.88 (m, 4H), 1.41 (s, 6H); m/z [M+H]$^+$=601.26.

Example 11

Evaluation of Efficacy of a Compound of Formula (Ia) in an Allergic Asthma Model Materials and Methods
Animal Preparation:

Compounds will be tested in the sheep model of experimental asthma reported in Abraham W M, Asthma & Rhinitis, 2000: 1205-1227 incorporated herein by reference in its entirety. All animals will be tested for both early and late stage airway responses to inhalation challenge with *Ascaris suum* antigen.

Measurement of Airway Mechanics:

The unsedated sheep will be restrained in a cart in the prone position with their heads immobilized. After topical anesthesia of the nasal passages with 2% lidocaine solution, a balloon catheter will be advanced through one nostril into the lower esophagus. The sheep will be intubated with a cuffed endotracheal tube through the other nostril. Pleural pressure will be measured using an esophageal balloon catheter. Lateral pressure in the trachea will be measured with a sidehole catheter (inner dimension, 2.5 mm) advanced through and positioned distal to the tip of the endotracheal tube. Transpulmonary pressure, the difference between tracheal and pleural pressure, will be measured with a differential pressure transducer catheter system. For the measurement of pulmonary resistance ($R_L$), the proximal end of the endotracheal tube will be connected to a pneumotachograph. The signals of flow and transpulmonary pressure will be sent to a computer for on-line calculation of $R_L$ from transpulmonary pressure, respiratory volume (obtained by digital integration) and flow. Analysis of 5-10 breaths will be used for the determination of $R_L$ in L×cm H$_2$O/L/S.

While the forgoing description illustrates certain preferred embodiments and examples of the inventions disclosed herein, the description also enables the practice of additional aspects, advantages, embodiments and modifications of those disclosed herein, as appreciated by a person of ordinary skill in the relevant technological field.

We claim:

1. A compound of Formula (I), or a pharmaceutically acceptable salt thereof:

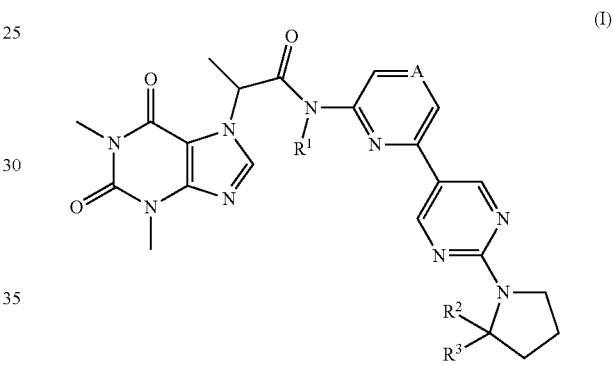

wherein,
R$^1$ is hydrogen or —CH$_2$—R$^{1a}$, wherein R$^{1a}$ is a phosphate moiety;
R$^2$ is CH$_3$;
R$^3$ is CH$_3$; and
A is N or CH.

2. The compound of claim 1, or a pharmaceutically acceptable salt thereof, wherein the compound of Formula (I) is a compound of Formula (Ia)

Formula (Ia)

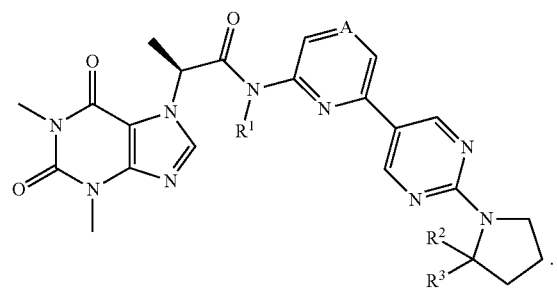

3. The compound of claim 1, or a pharmaceutically acceptable salt thereof, wherein A is CH.

4. The compound of claim 1, or a pharmaceutically acceptable salt thereof, wherein A is N.

5. A compound of Formula (I), or a pharmaceutically acceptable salt thereof:

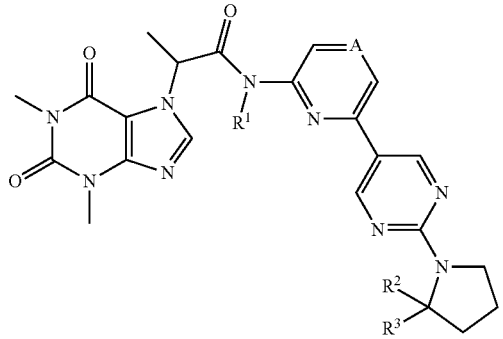

(I)

wherein,
- $R^1$ is hydrogen or —CH$_2$—$R^{1a}$, wherein $R^{1a}$ is a phosphate moiety;
- $R^2$ is hydrogen;
- $R^3$ is CH$_3$; and
- A is N.

6. A compound selected from:
(S)-2-(1,3-dimethyl-2,6-dioxo-1,2,3,6-tetrahydro-7H-purin-7-yl)-N-(6-(2-(2,2-dimethylpyrrolidin-1-yl)pyrimidin-5-yl)pyrazin-2-yl)propanamide,
(S)-2-(1,3-dimethyl-2,6-dioxo-1,2,3,6-tetrahydro-7H-purin-7-yl)-N-(6-(2-((S)-2-methylpyrrolidin-1-yl)pyrimidin-5-yl)pyrazin-2-yl)propanamide,
or a pharmaceutically acceptable salt thereof.

7. A compound of Formula (I), or a pharmaceutically acceptable salt thereof:

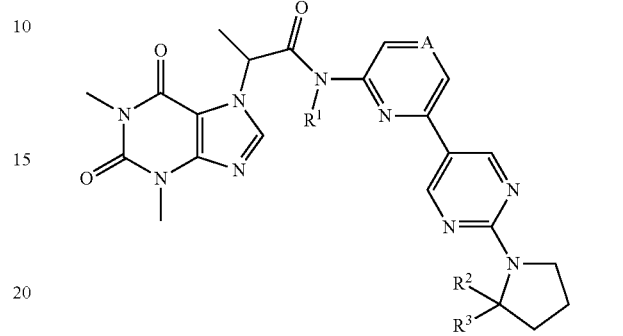

(I)

wherein,
- $R^1$ is hydrogen or —CH$_2$—$R^{1a}$, wherein $R^{1a}$ is a phosphate moiety;
- $R^2$ is hydrogen;
- $R^3$ is CH$_3$; and
- A is CH.

8. The compound of claim 7, or a pharmaceutically acceptable salt thereof, wherein $R^1$ is hydrogen.

* * * * *